(12) United States Patent
Tsao et al.

(10) Patent No.: US 10,463,709 B2
(45) Date of Patent: Nov. 5, 2019

(54) SHORT SYNTHETIC PEPTIDE FOR TREATING DISEASES AND/OR CONDITIONS RELATED TO ANGIOGENESIS

(71) Applicant: MacKay Memorial Hospital, Taipei (TW)

(72) Inventors: Yeou-Ping Tsao, Taipei (TW); Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 15/569,122

(22) PCT Filed: Apr. 14, 2016

(86) PCT No.: PCT/CN2016/079300
§ 371 (c)(1),
(2) Date: Oct. 25, 2017

(87) PCT Pub. No.: WO2016/173402
PCT Pub. Date: Nov. 3, 2016

(65) Prior Publication Data
US 2018/0099993 A1   Apr. 12, 2018

Related U.S. Application Data

(60) Provisional application No. 62/152,980, filed on Apr. 27, 2015.

(51) Int. Cl.
| | | |
|---|---|---|
| *A61K 38/08* | (2019.01) | |
| *C07K 7/06* | (2006.01) | |
| *C07K 14/00* | (2006.01) | |
| *A61P 7/06* | (2006.01) | |
| *A61P 17/10* | (2006.01) | |
| *A61P 27/02* | (2006.01) | |
| *A61P 17/06* | (2006.01) | |
| *A61P 21/00* | (2006.01) | |
| *A61P 21/04* | (2006.01) | |
| *A61P 19/06* | (2006.01) | |
| *A61P 25/28* | (2006.01) | |
| *A61P 1/16* | (2006.01) | |
| *A61P 11/06* | (2006.01) | |
| *A61P 37/06* | (2006.01) | |
| *A61P 17/00* | (2006.01) | |
| *A61P 19/02* | (2006.01) | |
| *A61P 37/08* | (2006.01) | |
| *A61P 3/10* | (2006.01) | |
| *A61P 1/00* | (2006.01) | |
| *A61P 11/00* | (2006.01) | |
| *A61P 25/00* | (2006.01) | |
| *A61P 25/16* | (2006.01) | |
| *A61P 29/00* | (2006.01) | |
| *A61P 1/04* | (2006.01) | |
| *A61P 9/14* | (2006.01) | |
| *A61K 45/06* | (2006.01) | |
| *A61P 27/06* | (2006.01) | |
| *A61P 9/10* | (2006.01) | |
| *A61P 31/00* | (2006.01) | |
| *A61P 9/00* | (2006.01) | |
| *A61P 27/04* | (2006.01) | |
| *A61P 31/12* | (2006.01) | |

(Continued)

(52) U.S. Cl.
CPC .............. *A61K 38/08* (2013.01); *A61K 45/06* (2013.01); *A61P 1/00* (2018.01); *A61P 1/04* (2018.01); *A61P 1/16* (2018.01); *A61P 3/10* (2018.01); *A61P 7/06* (2018.01); *A61P 9/00* (2018.01); *A61P 9/10* (2018.01); *A61P 9/14* (2018.01); *A61P 11/00* (2018.01); *A61P 11/06* (2018.01); *A61P 17/00* (2018.01); *A61P 17/06* (2018.01); *A61P 17/10* (2018.01); *A61P 19/02* (2018.01); *A61P 19/06* (2018.01); *A61P 21/00* (2018.01); *A61P 21/04* (2018.01); *A61P 25/00* (2018.01); *A61P 25/16* (2018.01); *A61P 25/28* (2018.01); *A61P 27/02* (2018.01); *A61P 27/04* (2018.01); *A61P 27/06* (2018.01); *A61P 29/00* (2018.01); *A61P 31/00* (2018.01); *A61P 31/04* (2018.01); *A61P 31/10* (2018.01); *A61P 31/12* (2018.01); *A61P 33/02* (2018.01); *A61P 35/00* (2018.01); *A61P 35/02* (2018.01); *A61P 35/04* (2018.01); *A61P 37/06* (2018.01); *A61P 37/08* (2018.01); *C07K 7/06* (2013.01); *C07K 14/001* (2013.01); *A61K 38/00* (2013.01)

(58) Field of Classification Search
None
See application file for complete search history.

(56) References Cited

U.S. PATENT DOCUMENTS

2010/0041614 A1* 2/2010 Bussolino .............. A61K 49/14
514/1.1

OTHER PUBLICATIONS

Pennigton et al., "Epidemiology of age-related macular degeneration (AMD): associations with cardiovascular disease phenotypes and lipid factors", Eye and Vision, 2016; 1-20 (Year: 2016).*

(Continued)

*Primary Examiner* — Lianko G Garyu

(57) ABSTRACT

Disclosed herein are synthetic peptides and compositions comprising the same, for the treatment and/or prophylaxis of a disease or a condition related to angiogenesis. Also disclosed herein are methods of treating and/or preventing a disease or a condition related to angiogenesis, by administering to a subject in need of such treatment a composition containing a therapeutically effective amount of a synthetic peptide of the present disclosure.

7 Claims, 14 Drawing Sheets
Specification includes a Sequence Listing.

(51) Int. Cl.
*A61P 35/02* (2006.01)
*A61P 31/04* (2006.01)
*A61P 33/02* (2006.01)
*A61P 35/04* (2006.01)
*A61P 31/10* (2006.01)
*A61P 35/00* (2006.01)
*A61K 38/00* (2006.01)

(56) References Cited

OTHER PUBLICATIONS

Centers for Disease Control and Prevention, "Watch Out for Diabetic Retinopathy", 2018, pp. 1-4, accessed https://www.cdc.gov/features/diabetic-retinopathy/index.html on Feb. 12, 2019 (Year: 2018).*

National Eye Institute, "Facts about Glaucoma", 2015, pp. 1-9; accessed https://nei.nih.gov/health/glaucoma/glaucoma_facts on Feb. 12, 2019 (Year: 2015).*

\* cited by examiner (A)

(B)

(A)

Vehicle          7-mer (B)

```
                        SEQUENCE LISTING

<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa is Ala, Asp, Asn, Leu, Phe or Val
<220> FEATURE:
<223> OTHER INFORMATION: X1X2X3X4X5X6X7
<220> FEATURE:
<221> NAME/KEY: VARIANT
<222> LOCATION: 2
<223> OTHER INFORMATION: Xaa is Ala, Ile, Leu or Val
<220> FEATURE:
<221> NAME/KEY: VARIANT
<222> LOCATION: 3
<223> OTHER INFORMATION: Xaa is Phe, Tyr or Trp
<220> FEATURE:
<221> NAME/KEY: VARIANT
<222> LOCATION: 4
<223> OTHER INFORMATION: Xaa is Arg or Lys
<220> FEATURE:
<221> NAME/KEY: VARIANT
<222> LOCATION: 5
<223> OTHER INFORMATION: Xaa is Val, Met, Ile, Leu or Gln
<220> FEATURE:
<221> NAME/KEY: VARIANT
<222> LOCATION: 6
<223> OTHER INFORMATION: Xaa is Arg, Gln, Lys or Pro
<220> FEATURE:
<221> NAME/KEY: VARIANT
<222> LOCATION: 7
<223> OTHER INFORMATION: Xaa is Ser or Thr

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: 7-mer

<400> SEQUENCE: 2

Asp Leu Tyr Arg Val Arg Ser
1               5

<210> SEQ ID NO 3
<211> LENGTH: 7
```

```
<212> TYPE: PRT
<213> ORGANISM: Artificial Sequence
<220> FEATURE:
<223> OTHER INFORMATION: 7-mer Da

<400> SEQUENCE: 3

Ala Leu Tyr Arg Val Arg Ser
1               5

<210> SEQ ID NO 4
<211> LENGTH: 7
<212> TYPE: PRT
<213> ORGANISM: Artificial Sequence
<220> FEATURE:
<223> OTHER INFORMATION: 7-mer La

<400> SEQUENCE: 4

Asp Ala Tyr Arg Val Arg Ser
1               5

<210> SEQ ID NO 5
<211> LENGTH: 7
<212> TYPE: PRT
<213> ORGANISM: Artificial Sequence
<220> FEATURE:
<223> OTHER INFORMATION: 7-mer Ya

<400> SEQUENCE: 5

Asp Leu Ala Arg Val Arg Ser
1               5

<210> SEQ ID NO 6
<211> LENGTH: 7
<212> TYPE: PRT
<213> ORGANISM: Artificial Sequence
<220> FEATURE:
<223> OTHER INFORMATION: 7-mer Ra

<400> SEQUENCE: 6

Asp Leu Tyr Ala Val Arg Ser
1               5

<210> SEQ ID NO 7
<211> LENGTH: 7
<212> TYPE: PRT
<213> ORGANISM: Artificial Sequence
<220> FEATURE:
<223> OTHER INFORMATION: 7-mer Va

<400> SEQUENCE: 7

Asp Leu Tyr Arg Ala Arg Ser
1               5

<210> SEQ ID NO 8
<211> LENGTH: 7
<212> TYPE: PRT
<213> ORGANISM: Artificial Sequence
<220> FEATURE:
<223> OTHER INFORMATION: 7-mer R2a

<400> SEQUENCE: 8

Asp Leu Tyr Arg Val Ala Ser
1               5

<210> SEQ ID NO 9
<211> LENGTH: 7
<212> TYPE: PRT
```

```
<213> ORGANISM: Artificial Sequence
<220> FEATURE:
<223> OTHER INFORMATION: 7-mer Sa

<400> SEQUENCE: 9

Asp Leu Tyr Arg Val Arg Ala
1               5

<210> SEQ ID NO 10
<211> LENGTH: 7
<212> TYPE: PRT
<213> ORGANISM: Artificial Sequence
<220> FEATURE:
<223> OTHER INFORMATION: 7-mer MK

<400> SEQUENCE: 10

Asp Leu Tyr Arg Met Lys Ser
1               5

<210> SEQ ID NO 11
<211> LENGTH: 7
<212> TYPE: PRT
<213> ORGANISM: Artificial Sequence
<220> FEATURE:
<223> OTHER INFORMATION: 7-mer KP

<400> SEQUENCE: 11

Asp Leu Tyr Lys Val Pro Ser
1               5

<210> SEQ ID NO 12
<211> LENGTH: 7
<212> TYPE: PRT
<213> ORGANISM: Artificial Sequence
<220> FEATURE:
<223> OTHER INFORMATION: 7-mer WI

<400> SEQUENCE: 12

Asp Leu Trp Arg Ile Arg Ser
1               5

<210> SEQ ID NO 13
<211> LENGTH: 7
<212> TYPE: PRT
<213> ORGANISM: Artificial Sequence
<220> FEATURE:
<223> OTHER INFORMATION: 7-mer IP

<400> SEQUENCE: 13

Asp Ile Tyr Arg Val Pro Ser
1               5

<210> SEQ ID NO 14
<211> LENGTH: 7
<212> TYPE: PRT
<213> ORGANISM: Artificial Sequence
<220> FEATURE:
<223> OTHER INFORMATION: 7-mer NV

<400> SEQUENCE: 14

Asn Val Tyr Arg Val Arg Ser
1               5

<210> SEQ ID NO 15
<211> LENGTH: 7
<212> TYPE: PRT
<213> ORGANISM: Artificial Sequence
```

```
<220> FEATURE:
<223> OTHER INFORMATION: 7-mer QK

<400> SEQUENCE: 15

Asp Leu Tyr Arg Gln Lys Ser
1               5

<210> SEQ ID NO 16
<211> LENGTH: 7
<212> TYPE: PRT
<213> ORGANISM: Artificial Sequence
<220> FEATURE:
<223> OTHER INFORMATION: 7-mer VFT

<400> SEQUENCE: 16

Asp Val Phe Arg Val Arg Thr
1               5

<210> SEQ ID NO 17
<211> LENGTH: 7
<212> TYPE: PRT
<213> ORGANISM: Artificial Sequence
<220> FEATURE:
<223> OTHER INFORMATION: 7-mer VL

<400> SEQUENCE: 17

Asp Leu Tyr Arg Leu Arg Ser
1               5

<210> SEQ ID NO 18
<211> LENGTH: 7
<212> TYPE: PRT
<213> ORGANISM: Artificial Sequence
<220> FEATURE:
<223> OTHER INFORMATION: 7-mer R2Q

<400> SEQUENCE: 18

Asp Leu Tyr Arg Val Gln Ser
1               5

<210> SEQ ID NO 19
<211> LENGTH: 7
<212> TYPE: PRT
<213> ORGANISM: Artificial Sequence
<220> FEATURE:
<223> OTHER INFORMATION: 7-mer DV

<400> SEQUENCE: 19

Val Leu Tyr Arg Val Arg Ser
1               5

<210> SEQ ID NO 20
<211> LENGTH: 7
<212> TYPE: PRT
<213> ORGANISM: Artificial Sequence
<220> FEATURE:
<223> OTHER INFORMATION: 7-mer DF

<400> SEQUENCE: 20

Phe Leu Tyr Arg Val Arg Ser
1               5

<210> SEQ ID NO 21
<211> LENGTH: 7
<212> TYPE: PRT
<213> ORGANISM: Artificial Sequence
<220> FEATURE:
```

```
<223> OTHER INFORMATION: 7-mer DL

<400> SEQUENCE: 21

Leu Leu Tyr Arg Val Arg Ser
1               5

<210> SEQ ID NO 22
<211> LENGTH: 6
<212> TYPE: PRT
<213> ORGANISM: Artificial Sequence
<220> FEATURE:
<223> OTHER INFORMATION: 6-mer

<400> SEQUENCE: 22

Asp Leu Tyr Arg Val Arg
1               5
```

SHORT SYNTHETIC PEPTIDE FOR TREATING DISEASES AND/OR CONDITIONS RELATED TO ANGIOGENESIS

CROSS-REFERENCE TO RELATED APPLICATIONS

This application is a national stage of PCT international Application No. PCT/CN2016/079300, filed on Apr. 14, 2016, and published in English on Nov. 3, 2016 with the Publication No. WO2016/173402A1, and claims priority to U.S. Provisional Patent Application No 62/152,980, filed Apr. 27, 2015, which is incorporated herein by reference in its entirety.

BACKGROUND OF THE INVENTION

1. Field of the Invention

The present disclosure relates to the discovery of a short synthetic peptide, and its use for the treatment and/or prophylaxis of diseases and/or conditions related to angiogenesis.

2. Description of Related Art

Angiogenesis is the formation, development and growth of new blood vessels. Typically, angiogenesis is tightly regulated and is governed by a fine balance between factors that induce the formation of blood vessels and those that halt or inhibit the process. When this balance is upset, it generally results in pathological angiogenesis. Pathological process associated with or induced by angiogenesis include diseases and/or conditions as diverse as cancers, vascular anomaly, infection, cardiovascular disease and injury.

Accordingly, there exists a need in the related filed of an improved medication and/or method for treating and/or preventing diseases and/or conditions related to angiogenesis.

SUMMARY OF THE INVENTION

In general, the present disclosure relates to the development of novel compounds and/or methods for treating diseases and/or conditions related to angiogenesis.

Accordingly, the first aspect of the present disclosure aims at providing a short synthetic peptide capable of treating diseases and/or conditions related to angiogenesis. The short synthetic peptide consists of 7 consecutive amino acid residues set forth as $X_1X_2X_3X_4X_5X_6 X_7$ (SEQ ID NO: 1), wherein, $X_1$ is alanine (A), aspartic acid (D), asparagine (N), leucine (L), phenylalanine (F), or valine (V);
$X_2$ is alanine (A), isoleucine (I), leucine (L), or valine (V);
$X_3$ is phenylalanine (F), tyrosine (Y) or tryptophan (W);
$X_4$ is arginine (R) or lysine (K);
$X_5$ is valine (V), methionine (M), isoleucine (I), leucine (L), or glutamine (Q);
$X_6$ is arginine (R), glutamine (Q), lysine (K) or proline (P);
$X_7$ is serine (S) or threonine (T); and
each $X_2$, $X_3$, $X_4$, $X_6$ and $X_7$ are independently L-form amino acid residues.

According to some preferred embodiments, at least one of $X_1$ and $X_5$ is a D-form amino acid residue, and the synthetic peptide has the amino acid sequence of SEQ ID NO: 2 (hereinafter 7-mer). In one example, $X_1$ is in D-form, such as D-aspartic acid (hereinafter 7-mer DD). In another example, $X_5$ is in D-form, such as D-valine (hereinafter 7-mer DV).

According to other preferred embodiments, the synthetic peptide has the amino acid sequence that is any of SEQ ID NOs: 3, 4, 10, 11, 12, 13, 14, 15, 16, 17, 18, 19, 20 or 21. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La). In yet another example, the synthetic peptide has the amino acid sequence of SEQ ID NO: 10 (herein after 7-mer MK). In a further example, the synthetic peptide has the amino acid sequence of SEQ ID NO: 11 (herein after 7-mer KP). In still a further example, the synthetic peptide has the amino acid sequence of SEQ ID NO: 12 (herein after 7-mer WI). In yet a further example, the synthetic peptide has the amino acid sequence of SEQ ID NO: 13 (herein after 7-mer IP). In another example, the synthetic peptide has the amino acid sequence of SEQ ID NO: 14 (herein after 7-mer NV). In yet another example, the synthetic peptide has the amino acid sequence of SEQ ID NO: 15 (herein after 7-mer QK). In a further example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→V)). In other example, the synthetic peptide has the amino acid sequence of SEQ ID NO: 20 (herein after 7-mer (D→F)). In a further example, the synthetic peptide has the amino acid sequence of SEQ ID NO: 21 (herein after 7-mer (D→L)).

The second aspect of the present disclosure aims at providing a medicament and/or a composition suitable for treating a disease and/or a condition related to angiogenesis. The medicament or composition comprises, an effective amount of the synthetic peptide described above, and a pharmaceutically acceptable carrier.

According to some preferred embodiments, at least one of $X_1$, and $X_5$ is a D-form amino acid residue, and the synthetic peptide has the amino acid sequence of SEQ ID NO: 2. In one example, $X_1$ is in D-form, such as D-aspartic acid (hereinafter 7-mer DD). In another example, $X_5$ is in D-form, such as D-valine (hereinafter 7-mer DV).

According to preferred embodiments, the synthetic peptide has the amino acid sequence that is any of SEQ ID NOs: 3, 4, 10, 11, 12, 13, 14, 15, 16, 17, 18, 19, 20, or 21. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La). In yet another example, the synthetic peptide has the amino acid sequence of SEQ ID NO: 10 (herein after 7-mer MK). In a further example, the synthetic peptide has the amino acid sequence of SEQ ID NO: 11 (herein after 7-mer KP). In still a further example, the synthetic peptide has the amino acid sequence of SEQ ID NO: 12 (herein after 7-mer WI). In yet a further example, the synthetic peptide has the amino acid sequence of SEQ ID NO: 13 (herein after 7-mer IP). In another example, the synthetic peptide has the amino acid sequence of SEQ ID NO: 14 (herein after 7-mer NV). In yet another example, the synthetic peptide has the amino acid sequence of SEQ ID NO: 15 (herein after 7-mer QK). In a further example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→V)). In other example, the synthetic peptide has the amino acid sequence of SEQ ID NO: 20 (herein after 7-mer (D→F)). IN a further example, the synthetic peptide has the amino acid sequence of SEQ ID NO: 21 (herein after 7-mer (D→L)).

The disease and/or condition related to angiogenesis treatable by the present medicament or composition is selected from the group consisting of, cancer, ocular disease, vascular anomaly, infection, cardiovascular disease and injury.

According to some embodiments, the present medicament or composition is suitable for treating cancer, which is any of breast cancer, cervical cancer, ovary cancer, endometrial cancer, melanoma, bladder cancer, lung cancer, pancreatic cancer, colon cancer, prostate cancer, hematopoietic tumors of lymphoid lineage, myeloid leukemia, thyroid cancer, thyroid follicular cancer, myelodysplastic syndrome (MDS), tumor of mesenchymal origin, melanoma, uveal melanoma, teratcarcinoma, neuroblastoma, glioma, glioblastoma, keratoacanthomas, renal cancer, analplastic large cell lymphoma, esophageal squamous cell carcinoma, heptatocellular carcinoma, follicular dentritic cell carcinoma, intestinal cancer, muscle invasive cancer, seminal vesicle tumor, epidermal carcinoma, spleen cancer, bladder cancer, head and neck cancer, stomach cancer, bone cancer, brain cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL).

The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). The tumor of mesenchymal origin is fibrosarcomas or rhabdomyosarcomas.

In some examples, the cancer is metastatic, preferably, the cancer is metastatic lung cancer.

In other examples, the cancer is uterine sarcoma.

According to some embodiments, the present medicament or composition is suitable for treating the ocular disease, which is any of corneal neovascularization, choroidal neovascularization (CNV), diabetic retinopathy, retinopathy of prematurity, age-related macular degeneration (AMD), juvenile macular degeneration, diabetic macular edema, retinitis pigmentosa, trachoma, glaucoma, dry eye syndrome, neuroophthalmic disease, retinal artery occlusion, uveitis, choroiditis, central serous chorioretinopathy (CSC), central exudative chorioretinopathy (CEC), polypoidal chorodial vasculopathy (PCV), neovascular glaucoma, neovascular maculopathy, or post-laser complications.

In one example, the ocular disease is age-related macular degeneration (AMD).

In another example, the ocular disease is diabetic retinopathy.

According to some embodiments, the present medicament or composition is suitable for treating vascular anomaly, which is selected from the group consisting of, vascular permeability, plasma leakage, venous malformation (VM), hemangioblastoma, hemangiomas, brain arteriovenous malformations (BAVM), arteriosclerosis, thrombosis, choroidal neovascularization (CNV), and Osler-Weber syndrome.

In one preferred example, the vascular anomaly is choroidal neovascularization (CNV), also termed wet type age-related macular degeneration (wet type age-related AMD).

According to further embodiments, the present medicament or composition is suitable for treating infection, which is a bacterial infection, virus infection, fungal infection, or protozoan infection.

According to further embodiments, the present medicament or composition is suitable for treating cardiovascular disease, which is selected from the group consisting of, atherosclerosis, myocardial angiogenesis, hyperviscosity syndromes, vein occlusion, artery occlusion, carotid obstructive disease, Osler-Weber-Rendu disease, myocarditis, cerebrovascular accident, mitral valve regurgitation, hypotension, arterial or post-transplantational artherosclerosis, fibrosis, thrombosis, and platelet aggregation.

According to other embodiments, the present medicament or composition is suitable for treating injury, which may be wound or trauma caused by accident or tissue transplant.

The medicament or composition of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathccal, perispinal, and intra-spinal) or parenteral (e.g., subcutaneous, intramuscular, intravenous, and intradermal), transmucosal administration or administration via an implant, or other delivery routes known in the art.

The third aspect of the present disclosure is thus directed to a method of treating a subject suffering from a disease and/or a condition related to angiogenesis. The method comprises the step of, administering to the subject a medicament or a composition of the present disclosure described above for ameliorating or alleviating symptoms related to the diseases and/or conditions related to angiogenesis.

According to preferred embodiments, the disease and/or condition related to angiogenesis treatable by the present method is selected from the group consisting of, cancer, ocular disease, vascular anomaly, infection, cardiovascular disease and injury.

According to preferred examples, the cancer that is treatable by the present method is selected from the group consisting of, breast cancer, cervical cancer, ovary cancer, endometrial cancer, melanoma, bladder cancer, lung cancer, pancreatic cancer, colon cancer, prostate cancer, hematopoietic tumors of lymphoid lineage, myeloid leukemia, thyroid cancer, thyroid follicular cancer, myelodysplastic syndrome (MDS), tumor of mesenchymal origin, melanoma, uveal melanoma, teratcarcinoma, neuroblastoma, glioma, glioblastoma, keratoacanthomas, renal cancer, analplastic large cell lymphoma, esophageal squamous cell carcinoma, heptatocellular carcinoma, follicular dentritic cell carcinoma, intestinal cancer, muscle invasive cancer, seminal vesicle tumor, epidermal carcinoma, spleen cancer, bladder cancer, head and neck cancer, stomach cancer, bone cancer, brain cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL).

The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). The tumor of mesenchymal origin is fibrosarcomas or rhabdomyosarcomas.

In some examples, the cancer is metastatic, preferably, the cancer is metastatic lung cancer.

In other examples, the cancer is uterine sarcoma.

According to some embodiments, the ocular disease may be any of corneal neovascularization, choroidal neovascularization (CNV), diabetic retinopathy, retinopathy of prematurity, age-related macular degeneration (AMD), juvenile macular degeneration, diabetic macular edema, retinitis pigmentosa, trachoma, glaucoma, dry eye syndrome, neuro-ophthalmic disease, retinal artery occlusion, uveitis, chorioiditis, central serous chorioretinopathy (CSC), central exudative chorioretinopathy (CEC), polypoidal chorodial vasculopathy (PCV), neovascular glaucoma, neovascular maculopathy, or post-laser complications.

In one example, the ocular disease is age-related macular degeneration (AMD).

In another example, the ocular disease is diabetic retinopathy.

According to some embodiments, the vascular anomaly may be selected from the group consisting of, vascular permeability, plasma leakage, venous malformation (VM), hemangioblastoma, hemangiomas, brain arteriovenous malformations (BAVM), arteriosclerosis, thrombosis, choroidal neovascularization (CNV), and Osler-Weber syndrome.

In one preferred example, the vascular anomaly is choroidal neovascularization (CNV).

According to further embodiments, the infection is any a bacterial infection, virus infection, fungal infection, or protozoan infection.

According to further embodiments, the cardiovascular disease is selected from the group consisting of, atherosclerosis, myocardial angiogenesis, hyperviscosity syndromes, vein occlusion, artery occlusion, carotid obstructive disease, Osler-Weber-Rendu disease, myocarditis, cerebrovascular accident, mitral valve regurgitation, hypotension, arterial or post-transplantational artherosclerosis, fibrosis, thrombosis, and platelet aggregation.

According to other embodiments, the injury may be wound or trauma caused by accident or tissue transplant.

In all embodiments, the subject is a human.

The details of one or more embodiments of the invention are set forth in the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present description will be better understood from the following detailed description read in light of the accompanying drawings, where.

DESCRIPTION OF THE INVENTION

Figure 1:
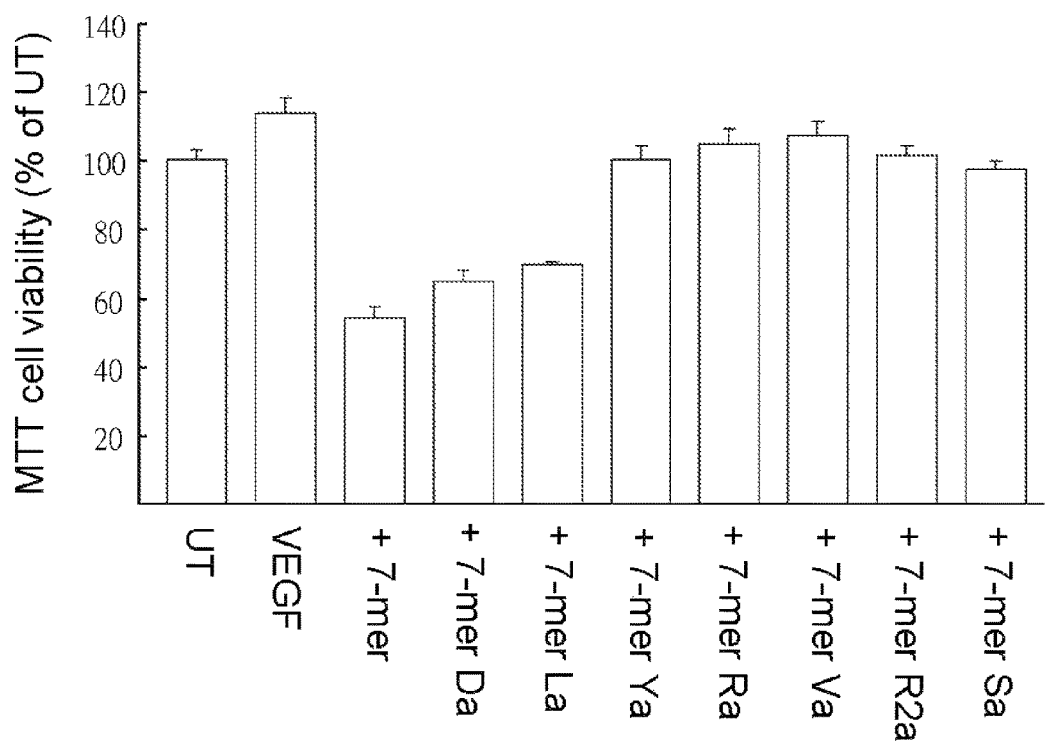
FIG. 1 is a bar graph illustrating the effects of the 7-mer analogues created by alanine scanning on the VEGF-induced proliferation of RPMI8226 cells in accordance with one embodiment of the present disclosure, three independent assays were performed, and data is presented as the mean±S.D.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of whole antigen or the like. Throughout the present disclosure, the positions of any specified amino acid residues within a peptide are numbered starting from the N terminus of the peptide. When amino acids are not designated as either D- or L-amino acids, the amino acid is either L-amino acid or could be either D- or L-amino acid, unless the context requires a particular isomer. The terms "D-amino acid" and "L-amino acid" are used to refer to absolute configuration of the amino acid, rather than a particular direction of rotation of plane-polarized light. The usage herein is consistent with standard usage by those skilled in the related art. Amino acids are designated herein using standard 1-letter or 3-letter codes, e.g., as designated in Standard ST.25 in the Handbook On Industrial Property Information and Documentation.

As discussed herein, minor variations in the amino acid sequences of proteins/peptides are contemplated as being encompassed by the presently disclosed and claimed inventive concept(s), providing that the variations in the amino acid sequence maintain at least 90%, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%. The present synthetic peptide may be modified specifically to alter a feature of the peptide unrelated to its physiological activity. For example, certain amino acids can be changed and/or deleted without affecting the physiological activity of the peptide in this study (i.e., its ability to treat angiogenesis related diseases and/or conditions). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains. In one example, one amino acid residue (e.g., valine) of the present synthetic peptide is conservatively replaced (e.g., by leucine). In other examples, two amino acid residues of the present synthetic peptide are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

The term "treatment" as used herein are intended to mean obtaining a desired pharmacological and/or physiologic effect, e.g., delaying or inhibiting cancer growth or ameliorating ischemic injury to an organ (e.g., brain). The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intraveneously, intramuscularly, intraperitoneally, intraarterially, intracranially, intraconjunctiva, or subcutaneously administering an agent (e.g., a compound or a composition) of the present invention.

The term "an effective amount" as used herein refers to an amount effective, at dosages, and for periods of time necessary, to achieve the desired result with respect to the treatment of a disease. For example, in the treatment of dry eye disease, an agent (i.e., a compound, a synthetic peptide, or a nucleic acid encoding a therapeutic peptide) which decrease, prevents, delays or suppresses or arrests any symptoms of the dry eye disease would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "subject" or "patient" is used interchangeably herein and is intended to mean a mammal including the human species that is treatable by the synthetic peptide and/or method of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "pharmaceutically acceptable carrier, excipient or stabilizer" as used herein is meant a suitable vehicle, agent or compound which is pharmaceutically acceptable for ophthalmic administration. As used herein, the term "ophthalmic composition" denotes a composition intended for application in the eye or intended for treating a device to be placed in contact with the eye, such as a contact lens.

As used herein, the term "diseases and/or conditions related to angiogenesis" means pathological diseases and/or conditions that involve up-regulated angiogenesis for the disease progression or symptom manifestation.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery of short synthetic peptides that are capable of treating and/or preventing a subject from developing a disease or a condition related to angiogenesis. Accordingly, this invention provides method and composition comprising the newly identified synthetic peptides for the treatment and/or prophylaxis of a disease or a condition related to angiogenesis.

2.1 The Present Synthetic Peptides

The short synthetic peptide of the present disclosure consists of 7 consecutive amino acid residues set forth as $X_1X_2X_3X_4X_5X_6 X_7$ (SEQ ID NO: 1), wherein, $X_1$ is alanine (A), aspartic acid (D), asparagine (N), leucine (L), phenylalanine (F), or valine (V);

$X_2$ is alanine (A), isoleucine (I), leucine (L), or valine (V);

$X_3$ is phenylalanine (F), tyrosine (Y) or tryptophan (W);

$X_4$ is arginine (R) or lysine (K);

$X_5$ is valine (V), methionine (M), isoleucine (I), leucine (L), or glutamine (Q);

$X_6$ is arginine (R), glutamine (Q), lysine (K) or proline (P);

$X_7$ is serine (S) or threonine (T); and each $X_2$, $X_3$, $X_4$, $X_6$ and $X_7$ are independently L-form amino acid residues.

According to some embodiments, at least one of $X_1$ and $X_5$ is a D-form amino acid residue, and the synthetic peptide has the amino acid sequence of SEQ ID NO: 2. In one example, $X_1$ is in D-form, such as D-aspartic acid (hereinafter 7-mer DD). In another example, $X_5$ is in D-form, such as D-valine (hereinafter 7-mer DV).

According to other preferred embodiments, the synthetic peptide has the amino acid sequence that is SEQ ID NOs: 3 or 4. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La).

According to other preferred embodiments, the synthetic peptide has the amino acid sequence that is any of SEQ ID NOs: 10, 11, 12, 13, 14, 15, 16, 17, 18, 19, 20 or 21. In one example, the synthetic peptide has the amino acid sequence of SEQ ID NO: 10 (herein after 7-mer MK). In another example, the synthetic peptide has the amino acid sequence of SEQ ID NO: 11 (herein after 7-mer KP). In yet another example, the synthetic peptide has the amino acid sequence of SEQ ID NO: 12 (herein after 7-mer WI). In a further example, the synthetic peptide has the amino acid sequence of SEQ ID NO: 13 (herein after 7-mer IP). In still a further example, the synthetic peptide has the amino acid sequence of SEQ ID NO: 14 (herein after 7-mer NV). In yet a further example, the synthetic peptide has the amino acid sequence of SEQ ID NO: 15 (herein after 7-mer QK). In another example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→V)). In other example, the synthetic peptide has the amino acid sequence of SEQ ID NO: 20 (herein after 7-mer (D→F)). IN a further example, the synthetic peptide has the amino acid sequence of SEQ ID NO: 21 (herein after 7-mer (D→L)).

According to some embodiments, serine (S) residues located at the C-terminus of SEQ ID NO: 2 is deleted, and the resulted peptide designated as the control peptide (DLYRVR, SEQ ID NO: 22) does not possess any biological function in the present study. Accordingly, serine (S) residue located at the C-terminus of SEQ ID NO: 2 is necessary for the biological activity of the present synthetic peptide for the treatment and/or prophylaxis of a disease and/or a condition related to angiogenesis, this residues can only be substituted by conservative amino acid residues, but may not be deleted.

According to some embodiments of the present disclosure, at least one D-form amino acid residues is included in SEQ ID NO: 2, which gives rise to D-form analogues of the 7-mer (i.e., 7-mer DD, and 7-mer DV) as described in the Table 1 of Example 1 of this application. Among these D-form analogues, it is found that tyrosine (Y), arginine (R) and serine (S) of the 7-mer (SEQ ID NO: 2) must remain in L-form, or else the resulted peptide (i.e., 7-mer DL, 7-mer DY, 7-mer DR, 7-mer DR2, and 7-mer DS, see Table 1 of Example 1) will lose its biological activity towards diseases and/or conditions related to angiogenesis, inflammation and/or fibrosis.

According to other embodiments of the present disclosure, each amino acid residues of the 7-mer are independently replaced by alanine (A), which give rise to 7-mer analogues (i.e., 7-mer Da, and 7-mer La) as described in the Table 1 of Example 1 of this application. Among these analogues, it is found that aspartic acid (D) and leucine (L) of the 7-mer (SEQ ID NO: 2) may be replaced by alanine (A) without losing its biological activity towards diseases and/or conditions related to angiogenesis, inflammation and/or fibrosis, whereas replacing any of the rest of amino acid residues of the 7-mer (i.e., amino acid residues at positions 3 to 7 of the 7-mer) results in the loss of the bioactivity of the 7-mer.

According to further embodiments of the present disclosure, at least two of the amino acid residues of the 7-mer are independently replaced by other amino acid residues, which give rise to 7-mer analogues (i.e., 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F) and 7-mer (D→L)) as described in the Table 1 of Example 1 of this application. It is found that each of the 7-mer analogues created by site specific replacement still possesses some level of bioactivity of the 7-mer peptide, among which, each of 7-mer VFT, 7-mer (V→L), 7-mer (D→V), 7-mer (D→F) and 7-mer (D→L) exhibits relatively the same bioactivity that is similar to the 7-mer (SEQ ID NO: 2).

The present synthetic peptide may be synthesized in accordance with any standard peptide synthesis protocol in the art. In one embodiment, the present synthetic peptides were synthesized by use of a solid-phase peptide synthesizer (ABI433A peptide synthesizer, Applied Biosystems Inc., Life Technologies Corp., Foster City, Calif., USA) in accordance with the manufacturer's protocols.

Alternatively, the present synthetic peptides may be prepared using recombinant technology. For example, one can clone a nucleic acid encoding the present peptide in an expression vector, in which the nucleic acid is operably linked to a regulatory sequence suitable for expressing the present peptide in a host cell. One can then introduce the vector into a suitable host cell to express the peptide. The expressed recombinant polypeptide can be purified from the host cell by methods such as ammonium sulfate precipitation and fractionation column chromatography. A peptide thus prepared can be tested for its activity according to the method described in the examples below.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The present synthetic peptide may be modified at its N-terminus or C-terminus. Examples of N-terminal modifications include, but are not limited to, N-glycated, N-alkylated, and N-acetylated amino acid. A terminal modification can include a pegylation. An example of C-terminal modification is a C-terminal amidated amino acid. Alternatively, one or more peptide bond may be replaced by a non-peptidyl linkage, the individual amino acid moieties may be modified through treatment with agents capable of reacting with selected side chains or terminal residues.

Various functional groups may also be added at various points of the synthetic peptide that are susceptible to chemical modification. Functional groups may be added to the termini of the peptide. In some embodiments, the function groups improve the activity of the peptide with regard to one or more characteristics, such as improving the stability, efficacy, or selectivity of the synthetic peptide; improving the penetration of the synthetic peptide across cellular membranes and/or tissue barrier; improving tissue localization; reducing toxicity or clearance; and improving resistance to expulsion by cellular pump and the like. Non-limited examples of suitable functional groups are those that facilitate transport of a peptide attached thereto into a cell, for example, by reducing the hydrophilicity and increasing the lipophilicity of the peptide, these functional groups may optionally and preferably be cleaved in vivo, either by hydrolysis or enzymatically, inside the cell. Hydroxy protecting groups include esters, carbonates and carbamate protecting groups. Amine protecting groups include alkoxy and aryloxy carbonyl groups. Carboxylic acid protecting groups include aliphatic, benzylic and aryl esters. In some optional embodiments, the carboxylic acid group in the side chain of the aspartic acid (D) of the present synthetic peptide is protected, preferably, by a methyl, ethyl, benzyl, or substituted benzyl ester.

A "peptidomimetic organic moiety" can optionally be substituted for amino acid residues in the present synthetic peptide both as conservative and as non-conservative substitutions. The peptidomimetic organic moieties optionally and preferably have steric, electronic or configuration properties similar to the replaced amino acid and such peptidomimetics are used to replace amino acids in the essential positions, and are considered conservative substitutions. Peptidomimetics may optionally be used to inhibit degradation of peptides by enzymatic or other degradative processes. The peptidomimetics can optionally and preferably be produced by organic synthetic techiniques. Non-limiting examples of suitable petidomimetics include isosteres of amide bonds, 3-amino-2-propenidone-6-carboxylic acid, hydroxyl-1,2,3,4-tetrahydro-isoquinoline-3-carboxylate, 1,2,3,4-tetrahydro-isoquinoline-3-carboxylate, and histidine isoquinolone carboxylic acid.

Any part of the synthetic peptide may optionally be chemically modified, such as by the addition of functional groups. The modification may optionally be performed during the synthesis of the present peptide. Non-limiting exemplary types of the modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxy groups to an amino group of a sugar. Acetal and ketal bonds can also optionally be formed between amino acids and carbon hydrates.

2.2 Compositions for the Treatment and/or Prophylaxis of Diseases and/or Conditions Related to Angiogenesis The present synthetic peptides are suitable for treating a subject suffering from a disease and/or a condition related to angiogenesis, or preventing a subject from developing the disease and/or condition related to angiogenesis.

Accordingly, a further aspect of the present disclosure is to provide a medicament comprising the present synthetic peptide for treating a disease and/or a condition related to angiogenesis, which include and are not limited to, cancer, ocular disease, vascular anomaly, infection, cardiovascular disease and injury.

In one embodiment, the medicament is for the treatment of cancer, in which after treatment, the volume, the growth rate, the metastasis, and/or the epithelial-to-mesenchymal transition (EMT) of the tumor are reduced or decreased. Non-limiting examples of cancer which may be treated by the medicament comprising the present synthetic peptide are solid tumors, sarcomas, hematological malignances, including but not limited to breast cancer, cervical cancer, ovary cancer, endometrial cancer, melanoma, bladder cancer, lung cancer, pancreatic cancer, colon cancer, prostate cancer, hematopoietic tumors of lymphoid lineage (e.g., leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (such as acute myelogenous leukemia (AML), chronic myelogenous leukemia), thyroid cancer, thyroid follicular cancer, myelodysplastic syndrome (MDS), tumors of mesenchymal origin (e.g., fibrosarcomas and rhabdomyosarcomas), melanoma, uveal melanoma, teratcarcinoma, neuroblastoma, glioma, glioblastoma, benign tumor of the skin (e.g., keratoacanthomas), renal cancer, analplastic large cell lymphoma, esophageal squamous cell carcinoma, heptatocellular carcinoma, follicular dentritic cell carcinoma, intestinal cancer, muscle invasive cancer, seminal vesicle tumor, epidermal carcinoma, spleen cancer, bladder cancer, head and neck cancer, stomach cancer, bone cancer, brain cancer, cancer of retina, biliary cancer, small bowel cancer, salivary gland cancer, cancer of uterus (e.g., uterine sarcoma), cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), and hereditary cancer syndrome (such as Li-Fraumeni syndrome and Von Hippel-Lindau syndrome (VHL)).

According to some examples, the cancer is metastatic. In one example, the cancer is metastatic lung cancer. In another example, the cancer is uterine sarcoma.

In another embodiment, the medicament is for the treatment of an ocular disease, which encompasses any disease, condition, or disorder of the eye (including its internal components such as eyelids, adnexa, conjunctive sclera, cornea, uvea, vitreous and retina, and optic nerves) and/or vision conditions and disorders. Non-limiting examples of the ocular diseases which may be treated by the medicament comprising the present synthetic peptide are ocular neovascularization (e.g., corneal neovascularization or choroidal neovascularization (CNV)), retinopathies (which include diabetic retinopathy, and retinopathy of prematurity), age-related macular degeneration (AMD), juvenile macular degeneration, diabetic macular edema, retinitis pigmentosa, trachoma, glaucoma, dry eye syndrome, neuro-ophthalmic disease, retinal artery occlusion, uveitis, choroiditis, central serous chorioretinopathy (CSC), central exudative chorioretinopathy (CEC), polypoidal chorodial vasculopathy (PCV), neovascular glaucoma, neovascular maculopathy, post-laser complications.

In one example, the ocular disease is age-related macular degeneration (AMD). In another example, the ocular disease is diabetic retinopathy.

In yet another embodiment, the medicament is for the treatment of a vascular anomaly, which encompasses any birthmark and/or vascular anomaly related disorder that may appear on any part of the body both externally or within the internal organs. Non-limiting examples of the vascular anomaly that may be treated by the medicament comprising the present synthetic peptide are vascular permeability, plasma leakage, venous malformation (VM), hemangioblastoma, hemangiomas, brain arteriovenous malformations (BAVM), arteriosclerosis, thrombosis, choroidal neovascularization (CNV), and Osler-Weber syndrome.

In one example, the vascular anomaly is choroidal neovascularization (CNV).

In yet a further embodiment, the medicament is for the treatment of cardiovascular disease, which encompasses any disease, disorder or condition of the heart and/or blood vessels. Non-limiting examples of the cardiovascular disease that may be treated by the medicament comprising the present synthetic peptide are atherosclerosis, myocardial angiogenesis, hyperviscosity syndromes, vein occlusion, artery occlusion, carotid obstructive disease, Osler-Weber-Rendu disease, myocarditis, cerebrovascular accident, mitral valve regurgitation, hypotension, arterial or post-transplantational artherosclerosis, fibrosis, thrombosis, and platelet aggregation.

In still a further embodiment, the medicament is for the treatment of infection caused by a bacterial infection, virus infection, fungal infection, or protozoan infection.

In other embodiment, the medicament is for the treatment of an injury, such as a wound or a trauma caused by accident or tissue transplant.

The medicament is manufactured by mixing suitable amount of the present synthetic peptide with a pharmaceutically acceptable carrier, excipient or stabilizer into a composition. In particular embodiments, the synthetic peptide is selected from the group of peptides as described above, which include but are not limited to, 7-mer, 7-mer DD, 7-mer DV, 7-mer Da, 7-mer La, 7-mer MK, 7-mer KP, 7-mer WI, 7-mer IP, 7-mer NV, 7-mer V→L, 7-mer QK, 7-mer LQ, 7-mer VFT, and a combination thereof.

The amount of the peptide present in the medicament or the composition will depend on the peptide used. The peptide typically will be present in the composition in the amount from about 0.001% to about 10% by weight, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0% by weight; in particular in an amount from about 0.01% to about 5% by weight, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0% by weight.

Pharmaceutical acceptable carriers, excipients or stabilizers for use with the synthetic peptides are well known in the relevant art, and include but are not limited to non-toxic inert solid, semi-solid, or liquid filler, diluent, encapsulating agent or formulation auxiliary. Typical pharmaceutically acceptable carrier is water or physiological saline. Examples of pharmaceutically acceptable carriers include, but are not limited to, sugars such as lactose, glucose, and sucrose; starches such as corn starch; cellulose and its derivatives such as carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; as well as other agents such as non-toxic lubricants (e.g., lauryl sulfate and magnesium stearate), coloring agents, releasing agents, flavoring agents, preservatives and antioxidants.

Suitable routes of administration of the medicament or the composition of the present invention are intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

Pharmaceutical composition suitable for oral administration may be formulated into discrete dosage units such as pills, tablets, lozenges or hard or soft capsules, or as a dispersible powder or granules, or as a solutions or suspension for example, aqueous or oily suspensions, emulsions, syrups, elixirs, or enteral formulas. The composition may be presented in uni-dose or multi-dose containers, such as sealed vials or ampoules, and may be stored in a lyophilized condition requiring the addition of sterile liquid carrier (e.g., water or saline) prior to use.

Pharmaceutical composition suitable for parental administration may be formulated into aqueous or non-aqueous sterile injection by mixing or dispersing the present synthetic peptide with a sterile solvent, such as water, Ringer's solution, saline, 1,3-butanediol, alcohol and etc. Alternatively, fixed oil, fatty acid or synthetic mono- or diglycerides may be used as the solvent. The composition may be sterilized by filtering through a filter.

For topical or transdermal application, the pharmaceutical composition is generally formulated into ointments, pastes, creams, lotions, gels, patches or sprays. Ophthalmic formulations, ear drops, and eye drops are also contemplated within the scope of the invention. According to some embodiments, compositions of the invention are administered topically to the eye. Depending on the type and severity of the disease, about 1 µg/kg to about 50 mg/kg (e.g., 0.1-20 mg/kg) of the present synthetic peptide is administered to the patient. A typical daily or weekly dosage might range from about 1 µg/kg to about 20 mg/kg or more. The doses utilized for any of the above-described purposes of topical administration will generally be from about 0.01 to about 100 mg per kilogram of body weight (mg/kg), administered one to several, e.g., four, six, eight or even more, times per day.

Pharmaceutical composition suitable for pulmonary administration is formulated as find dusts or mists which may be generated by means of metered dose pressurized aerosols, nebulisers or insufflators.

The pharmaceutical composition provided by the invention preferably is presented in the form of a kit. In the present invention, a "kit" is understood as a product containing the synthetic peptide(s) provided by the present invention and/or the additional therapeutic compounds forming the packaged composition such that the transport, storage and simultaneous or successive administration thereof is allowed. Therefore, the kits of the invention can contain one or more sealed ampoules respectively contain the synthetic peptides of the invention, and which can be prepared in a single dose or as multiple doses. The kit can additionally contain a vehicle suitable for solubilizing the synthetic peptides such as aqueous media such as saline solution, Ringer's solution, dextrose and sodium chloride; water-soluble media such as alcohol, polyethylene glycol, propylethylene glycol; and water-insoluble vehicles if necessary. Another component which may be present in the kit is a package which allows maintaining the compositions of the invention within determined limits. Materials suitable for preparing such packages include glass, plastic (polyethylene, polypropylene, polycarbonate and the like), bottles, vials, paper, sachets and the like.

The kit of the invention can additionally contain instructions for the simultaneous, successive or separate administration of the different formulations present in the kit. Therefore, the kit of the invention can further comprise instructions for the simultaneous, successive or separate administration of the different components. Said instructions can be in the form of printed material or in the form of an electronic support which can store the instructions such that they can be read by a subject, such as electronic storage media (magnetic disks, tapes and the like), optical media (CD-ROM, DVD) and the like. The media can additionally or alternatively contain Internet webpages providing said instructions.

2.3 Methods for the Treatment and/or Prophylaxis of Diseases and/or Conditions Related to Angiogenesis As it has been indicated above, the findings described in the present invention are useful for the prevention and/or treatment of diseases and/or conditions related to angiogenesis.

The present invention therefore relates to a method for the prevention and/or treatment of diseases and/or conditions related to angiogenesis, which comprises administering to a subject in need thereof a medicament or a composition described above, which comprises a synthetic peptide consisting of 7 consecutive amino acid residues set forth as $X_1X_2X_3X_4X_5X_6X_7$ (SEQ ID NO: 1), wherein, $X_1$ is alanine (A), aspartic acid (D), asparagine (N), leucine (L), phenylalanine (F), or valine (V);

$X_2$ is alanine (A), isoleucine (I), leucine (L), or valine (V);

$X_3$ is phenylalanine (F), tyrosine (Y) or tryptophan (W);

$X_4$ is arginine (R) or lysine (K);

$X_5$ is valine (V), methionine (M), isoleucine (I), leucine (L), or glutamine (Q);

$X_6$ is arginine (R), glutamine (Q), lysine (K) or proline (P);

$X_7$ is serine (S) or threonine (T); and each $X_2$, $X_3$, $X_4$, $X_6$ and $X_7$ are independently L-form amino acid residues; and a pharmaceutically acceptable carrier. The medicament and/or composition when administrated to the subject is capable of ameliorating or alleviating the symptoms associated to the diseases and/or conditions related to angiogenesis.

In particular embodiments, the synthetic peptide is selected from the group of peptides described above, which include and are not limited to, 7-mer, 7-mer DD, 7-mer DV, 7-mer Da, 7-mer La, 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F), 7-mer (D→L), and a combination thereof.

The diseases and/or conditions related to angiogenesis include, and are not limited to, cancer, ocular disease, vascular anomaly, infection, and cardiovascular disease.

According to one embodiment, the present invention is related to a method for treating cancer, which comprises administering to a subject in need thereof a medicament or a composition of the present invention. Non-limiting examples of cancer which may be treated by the present method are solid tumors, sarcomas, hematological malignances, including but not limited to breast cancer, cervical cancer, ovary cancer, endometrial cancer, melanoma, bladder cancer, lung cancer, pancreatic cancer, colon cancer, prostate cancer, hematopoietic tumors of lymphoid lineage (e.g., leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (such as acute myelogenous leukemia (AML), chronic myelogenous leukemia), thyroid cancer, thyroid follicular cancer, myelodysplastic syndrome (MDS), tumors of mesenchymal origin (e.g., fibrosarcomas and rhabdomyosarcomas), melanoma, uveal melanoma, teratcarcinoma, neuroblastoma, glioma, glioblastoma, benign tumor of the skin (e.g., keratoacanthomas), renal cancer, analplastic large cell lymphoma, esophageal squamous cell carcinoma, heptatocellular carcinoma, follicular dentritic cell carcinoma, intestinal cancer, muscle invasive cancer, seminal vesicle tumor, epidermal carcinoma, spleen cancer, bladder cancer, head and neck cancer, stomach cancer, bone cancer, brain cancer, cancer of retina, biliary cancer, small bowel cancer, salivary gland cancer, cancer of uterus (e.g., uterine sarcoma), cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), and hereditary cancer syndrome (such as Li-Fraumeni syndrome and Von Hippel-Lindau syndrome (VHL)). In one example, the cancer is metastatic, such as metastatic lung cancer. In another example, the cancer is uterine sarcoma.

According to another embodiment, the present invention is related to a method for treating an ocular disease, which comprises administering to a subject in need thereof a medicament or a composition of the present invention. Non-limiting examples of the ocular disease treatable by the present method are ocular neovascularization (e.g., corneal neovascularization or choroidal neovascularization (CNV)), retinopathies (which include diabetic retinopathy, and retinopathy of prematurity), age-related macular degeneration (AMD), juvenile macular degeneration, diabetic macular edema, retinitis pigmentosa, trachoma, glaucoma, dry eye syndrome, neuro-ophthalmic disease, retinal artery occlusion, uveitis, choroiditis, central serous chorioretinopathy (CSC), central exudative chorioretinopathy (CEC), polypoidal chorodial vasculopathy (PCV), neovascular glaucoma, neovascular maculopathy, or post-laser complications. In one example, the ocular disease is CNV. In another example, the ocular disease is AMD. In still another example, the ocular disease is diabetic retinopathy.

According to another embodiment, the present invention is related to a method for treating a vascular anomaly, which comprises administering to a subject in need thereof a medicament or a composition of the present invention. Non-limiting examples of the vascular anomaly treatable by the present method are vascular permeability, plasma leakage, venous malformation (VM), hemangioblastoma, hemangiomas, brain arteriovenous malformations (BAVM), arteriosclerosis, thrombosis, choroidal neovascularization (CNV), and Osler-Weber syndrome. In one example, the vascular anomaly is CNV.

According to a further embodiment, the present invention is related to a method for treating a cardiovascular disease, which comprises administering to a subject in need thereof a medicament or a composition of the present invention. Non-limiting examples of the cardiovascular disease treatable by the present method are atherosclerosis, myocardial angiogenesis, hyperviscosity syndromes, vein occlusion, artery occlusion, carotid obstructive disease, Osler-Weber-Rendu disease, myocarditis, cerebrovascular accident, mitral valve regurgitation, hypotension, arterial or post-transplantational artherosclerosis, fibrosis, thrombosis, and platelet aggregation.

According to a further embodiment, the present invention is related to a method for treating an infection caused by a bacterial infection, virus infection, fungal infection, or protozoan infection.

According to other embodiment, the present invention is related to a method for the treatment of an injury, such as a wound or a trauma caused by accident or tissue transplant. The method includes the step of, administering to a subject in need thereof a medicament or a composition of the present invention.

Optionally, the present method may further include administering to the subject an effective amount of an agent selected from the group consisting of an anti-inflammatory agent, an anti-cancer agent, an antibiotic, and an anti-lymphangiogenic agent, for treating diseases and/or conditions related to angiogenesis.

In some examples, the anti-inflammatory agent may be cyclosporine. The anti-cancer agent may be an alkylating agent, an anti-microtubule agent, a topoisomerase inhibitor, or a cytotoxic agent. The antibiotic may be selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleanodomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline. The anti-lymphangiogenic agent may be a vascular endothelial growth factor C (VEGF-C) antibody, a VEGF-D antibody or a VEGF-3 antibody.

In all embodiments, the subject suitable for treatment is a human.

The present invention will now be described more specifically with reference to the following embodiments, which are provided for the purpose of demonstration rather than limitation.

EXAMPLES

Materials and Methods

Materials 3-(4,5-cimethylthiazol-2-yl)-2,5-diphenyl tetrazolium bromide (MTT) was from Merck (Catalog number 1.11714.0001). Vascular endothelial growth factor (VEGF), bFGF, TACS annexin V-FITC kit were purchased from R&D Systems (Minneapolis, Minn., USA). Matrigel was purchased from BD Biosciences (New Bedford, Mass., USA). HUVECs were purchased from Cascade Biologics, Inc. (Portland, Oreg., USA). Hydron (529265), sucrose octasulfate-aluminum complex (S0652), streptozotocin (STZ; S0130), fluorescein isothiocyanate-bovine serum albumin (FITC-BSA), were from Sigma-Aldrich (St. Louis, Mo., USA). RPMI1640 medium, trypsin-EDTA, fetal bovine serum (FBS), antibiotic-antimicotic solutions and trypsin were purchased from Invitrogen (Carlsbad, Calif., USA). Medium 200, LSGS Kit, fetal bovine serum (FBS) and Dulbecco's Modified Eagle Medium (DMEM) were all from Gibco-BRL.

All peptides were synthesized by GenScript (Piscataway, N.J., USA), in which each peptide was modified by acetylation at the $NH_2$ termini and amidation at the COOH termini to improve its stability, and was subsequently characterized using mass spectrometry (>95% purity).

Cell Culture and Treatment

HUVECs ($1 \times 10^5$ cells per well of 6-well plate) were grown in Medium 200 with Low Serum Growth Supplement (LSGS Kit, supplement contains 1.9% FBS, 3 ng/ml bFGF, 10 µg/ml heparin, 1 µg/ml hydrocortisone, and 10 ng/ml EGF). Culture plates were coated with 2% gelatin. Cells (passages 4-8) were cultured at 37° C. in a humidified atmosphere of 5% $CO_2$. For peptide treatment, HUVECs were cultured in low serum (0.5% FBS) media containing 10-20 ng/ml VEGF and 100 nM the present synthetic peptide.

Murine B16-F10 melanoma cells were cultured in DMEM containing 10% FBS, 2 mM L-glutamine, 100 U penicillin, 100 µg/ml streptomycin at 37° C. and 5% $CO_2$. The cells were used at passages 3-10.

Human WSI fibroblasts were grown in Eagle's Minimum essential Medium supplemented with 10% FBS at 37° C. in a humidified atmosphere of 5% $CO_2$.

The multiple myeloma line RPMI8226 was cultivated in complex medium (RPMI1640) supplemented with 10% (vol/vol) heat-inactivated fetal calf serum (Invitrogen), 50 µg/mL penicillin, 50 µg/mL streptomycin, and 2 mM L-glutamine at 37° C. in a 5% $CO_2$ atmosphere.

MTT Assay

RPMI8226 cells were cultured in serum-free RPMI1640 medium for 24 hrs, and then cells were seeded in 48-well culture plates ($3 \times 10^5$ cells/well) and continued to culture in 0.5 ml fresh serum-free RPMI1640 medium containing 25 µM peptide for another 24 hrs. The cell viability was determined by the MTT assay.

Briefly, 50 µL of MTT stock solution (50 µL) (5 mg MTT dissolved in 1 ml of sterile PBS) was added to each culture well. In addition, 50 µL of the MTT stock solution was added in 500 µL of medium as the negative control. The culture plate was incubated at 37° C. for 4 hours. Aliquots (450 µl) from each sample were taken to a new well of 48-well culture plate, adding 100 µL DMSO, mixing thoroughly using the pipette and reacted at 37° C. for 20 min and read absorbance at 570 nm.

VEGF-induced HUVEC Proliferation Assay

HUVECs ($1 \times 10^5$ cells per well of 6-well plate) in Medium 200 supplemented with LSGS Kit were allowed to grow onto 6-well plates coated with 2% gelatin for 24 hours at 37° C. in 5% $CO_2$. The culture medium was then replaced with serum free Medium 200 overnight. Cells were then treated with 100 nM the present synthetic peptide dissolved in Medium 200 plus 0.5% FBS and VEGF (10 ng/ml) for 24 hours at 37° C. Then, cells were harvested by trypsin-EDTA and counted using a hemocytometer.

Endothelial Cell Capillary-like Tube Formation Assay

To examine the effect of the present synthetic peptide on in vitro angiogenesis, growth factor-reduced matrigel was pipetted into pre-chilled 24-well plates (150 µl matrigel per well) and polymerized for 45 min at 37° C. HUVEC ($4 \times 10^4$ per well) suspended in low serum (0.5% FBS) media containing 20 ng/ml VEGF were seeded in the presence of the present synthetic peptide or the control peptide (SEQ ID NO: 22) (10 µM) in matrigel coated plates, and incubated for 6 hr, then tubular structures were photographed. In this experiment, images were captured using a Cannon camera on Zeiss inverted microscope with magnification ×40 and tube length was quantified using Image analysis software (Image-Pro Plus). The control peptide as used in the present invention has the sequence of DLYRVR (SEQ ID NO: 10).

Apoptotsis Assay

The percentage of apoptotic HUVEC cells was assayed using TACS annexin V-FITC kit. The percentage of annexin V-positive cells was determined using in situ staining according to the manufacturer's instruction. The cell number was determined by counterstaining with Hoechst 33342. The nuclei in ten randomly selected fields of the three different chambers (~7200 cells) were counted. Specimens were examined and photographed on a Zeiss epifluorescence microscope (×100, 10 fields/sample). Pictures were recorded on Zeiss software.

Rat Aortic Ring Assay

Thoracic aortas were removed from euthanized 10-week-old male Sprague Dawley rats, and gently stripped off periaortic fibroadipose tissue. Aortas were sectioned to about 2-mm length rings, which were embedded in Matrigel. To induce angiogenesis, human recombinant bFGF (50 ng/ml) or bFGF plus the peptide (50 µM) was added in Matrigel. Gel (200 µl) containing an aortic ring was polymerized in 12-well plates (37° C. for 30 min) and then incubated with 1 ml of Medium 200 supplemented with 100 units/ml penicillin, and 100 ng/ml streptomycin and 2% FBS at 37 ° C. The cultures were propagated at 37 ° C. in a humidified incubator for up to 7 days. Sprouts were recorded using an inverted microscope platform (Leica DM16000B) with bright-field optics. Each ring was scored by three independent observers on a scale 0-4 depending on the degree of sprouting vessel being observed (0=no sprouting, 4=profuse sprouting). The experiment was repeated in triplicates.

Experimental Animals

All animals were maintained in the animal facility in accordance with the procedures approved by Mackay Memorial Hospital Review Board (Taiwan, R.O.C.). All animal experimental procedures were conducted according to the ARVO Statement for the Use of Animals in Ophthalmic and Vision Research.

Mouse Corneal Angiogenesis Assay

Briefly, corneal micropockets were created on 6-week-old C57BL/6 mice by use of a needle. A micropellet of sucrose aluminum sulfate and hydron polymer containing 200 ng VEGF with or without 2.5 μg peptide was plated into each corneal pocket. Eyes were then photographed by a slit-lamp biomicroscope on day 7 after micropellet implantation. Ingrowth of the blood vessels into avascular cornea toward pellet was scored as positive response. The results were reported as positive corneas of total implant.

Tumorigenicity Assay

MES-SA/Dx5 cells ($5\times10^6$ cells in 0.1 ml) were implanted by subcutaneous injections in the right flank region of female nude mice (n=24, each animal weighted about 20 g before the assay began). The experiments were approved by the Mackay Memorial Hospital Review Board for animal investigation. Treatment was initiated in animals when the tumor volume was above 80 mm$^3$. Vehicle DMSO, the present synthetic peptide or the control peptide (10 mg/kg) was administered by intraperitoneal injections every 2 days. Tumor progression was monitored for 10 days; size of the tumor was measured every 3 to 5 days with a caliper and the volume was calculated using the following formula: ½×length×width$^2$.

Assay for Experimental Pulmonary Metastasis in Mice $2\times10^5$ B16-F10 cells were suspended in 100 μl PBS and checked for viability using trypan blue staining (>95%). The B16-F10 cells were then injected into the tail vein of the 6-week-old female C57BL/6 mice; while vehicle (DMSO), the present synthetic peptide or the control peptide (10 mg/kg) were administered by intraperitoneal injections every 2 days after the B16-F10 cell injection. Five mice were used for each group. On day 8 after inoculation of cells, the lungs were removed, and the number of visible colonies on the surface of the lungs were counted using a dissecting microscope.

Measurement of Vascular Abnormalities in the Retina of Diabetic Mice

Diabetic mice were generated by a single intraperitoneal injection of streptozotocin (STZ) (150 mg/kg body weight). STZ was freshly prepared in 0.1 M citrate buffer (pH 4.5). After injection, mice were supplied with 10% sucrose overnight to prevent sudden hypoglycemic shock. After 1 week, mice with non-fasting blood glucose levels >500 mg/dl were defined as diabetic and used for the experiments. DMSO Vehicle or the present synthetic peptide (10 mg/kg; n≥3 per peptide) were administered by intraperitoneal injections twice a day. After treatment for 24 h, mice were intraperitoneal injected with 100 mg/kg of BSA-FITC for further 30 min.

To determine vascular lesions (hemorrhaging areas) in retina, the animals were euthanized by $CO_2$ inhalation, and the eyes were enucleated and fixed by 2% paraformaldehyde for 2 hr and flat-mounted onto glass slides to obtain optical sections by an epifluorescence microscopy. Vascular lesions in the retina was scored in all four retinal quadrants of flat mounts by using a 20× objective. Six microscopic fields were sampled in each quadrant in both the central and peripheral retina, and data were presented as the average number of lesions/retina.

Vascular FITC-BSA leakage was determined by a fluorescence spectrofluorometer based on standard curves of FITC-BSA at excitation and emission wavelengths of 488 and 535 nm, respectively, and then normalized to a non-injected control retina. For this analysis, retinas were dissected from treated and untreated diabetic mice after BSA-FITC injections, and each was solubilized in 300 μL ice-cold PBS.

Measurement of Vascular Abnormalities in the Retina of Diabetic Rats

Diabetes was induced in male Sprague-Dawley rats after fasting overnight by a single intraperitoneal injection of STZ (65 mg/kg body weight). STZ was freshly prepared in 0.1 M citrate buffer (pH 4.5). Rats with blood glucose levels >350 mg/dl for 5 days after receiving STZ were considered to be in diabetic status and were termed diabetic rats hereinafter. Blood glucose levels were checked every 2 days a blood glucose monitor. Animals that served as non-diabetic controls received an equivalent amount of citrate buffer alone. For peptide treatment, diabetic rats were anesthetized by an intraperitoneal injection of a Xylazine (10 mg/kg), and then intravitreally injected with 3 μl of the present synthetic peptide (10 mM) into one eye and an equal volume of PBS was injected into the contralateral eye (n=3-6 per group). After peptide treatment for 24 h, measurement of retinal vascular leakage by BSA-FITC (100 mg/kg body weight) was conducted in according to procedures described above.

Laser Induced Choroidal Neovascularization (CNV)

The 8-week-old female C57BL/6 mice were anaesthetized by injecting intraperitoneally a mixture of zoletil (6 mg/kg) and xylazine (3 mg/kg). The retina was viewed through a slit lamp microscope, and the optic nerve head was placed in the center of the microscope field. Both eyes received 3 or 4 laser burns around the optic nerve head using the diode laser (lesion diameter 50 μm; duration 100 ms; energy 250 mW). The formation of a blister indicates rupture of the Bruch's membrane after laser application. DMSO Vehicle or 7-mer (10 mg/kg; n≥10 per peptide) were administered by intraperitoneal injections twice a day for 10 days. Fluorescein fundus images were taken about 5 minutes after intraperitoneal injection of 0.1 mL of 100 mg/ml Fluorescein (10% w/v). During this period, the size of fluorescein leakage spots was relatively stable. The leakage of each CNV lesion was graded by a retina specialist according to the method described by Sheets et al. (Molecular Vision 2010; 16:320-329). Briefly, The terms Grade 0, Grade 1, Grade 2a, and Grade 2b are respectively defined as follows: Grade 0, no hyperfluorescence; Grade 1, hyperfluorescence without leakage; Grade 2a, hyperfluorescence and late leakage; Grade 2b, bright hyperfluorescence and late leakage beyond treated areas.

Statistics

Results were expressed as the mean±standard error of the mean (SEM). 1-way ANOVA was used for statistical comparisons. $P<0.05$ was considered significant.

Example 1

Identification of the Functional Residues of the Present Synthetic Peptide

In this example, a 7-mer peptide (SEQ ID NO: 2) was synthesized in accordance with the procedures described in the "Materials and Methods" section. Analogues of the 7-mer were created by "alanine scanning," "D-amino acid substitution" or site specific replacement, in which each indicated residues was replaced by alanine, its D-form counterpart or by replacing with specific amino acid residuet.

Total of 25 peptides were synthesized, specifically, 7 analogues were created by "alanine scanning," they were termed 7-mer Da, 7-mer La, 7-mer Ya, 7-mer Ra, 7-mer Va, 7-mer R2a, and 7-mer Sa; and 7 analogues were created by "D-amino acid substitution," they were termed 7-mer DD, 7-mer DL, 7-mer DY, 7-mer DR, 7-mer DV, 7-mer DR2, and 7-mer DS; and additional 12 analogues were created by site specific replacement, they were termed 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F), and 7-mer (D→L). Furthermore, a 6-mer control peptide was also synthesized, in which the serine (S) residue of the 7-mer was deleted. The respective sequences of the synthesized peptides of this example (i.e., 7-mer and its analogues) were listed below in Table 1.

TABLE 1

The present synthetic peptides

| Peptide Name. | Amino Acid Sequence | SEQ ID NO |
|---|---|---|
| 7-mer | NH$_2$-Asp-Leu-Tyr-Arg-Val-Arg-Ser-COOH<br>DLYRVRS | 2 |
| *7-mer analogues created by "D-amino acid substitution"* | | |
| 7-mer DD | NH$_2$-(D-Asp)-Leu-Tyr-Arg-Val-Arg-Ser-COOH<br>DLYRVRS | 2 |
| 7-mer DL | NH$_2$-Asp-(D-Leu)-Tyr-Arg-Val-Arg-Ser-COOH<br>DLYRVRS | 2 |
| 7-mer DY | NH$_2$-Asp-Leu-(D-Tyr)-Arg-Val-Arg-Ser-COOH<br>DLYRVRS | 2 |
| 7-mer DR | NH$_2$-Asp-Leu-Tyr-(D-Arg)-Val-Arg-Ser-COOH<br>DLYRVRS | 2 |
| 7-mer DV | NH$_2$-Asp-Leu-Tyr-Arg-(D-Val)-Arg-Ser-COOH<br>DLYRVRS | 2 |
| 7-mer DR2 | NH$_2$-Asp-(D-Leu)-Tyr-Arg-Val-(D-Arg)-Ser-COOH<br>DLYRVRS | 2 |
| 7-mer DS | NH$_2$-Asp-Leu-Tyr-Arg-Val-Arg-(D-Ser)-COOH<br>DLYRVRS | 2 |
| *7-mer analogues created by "alanine scanning"* | | |
| 7-mer Da | NH$_2$-Ala-Leu-Tyr-Arg-Val-Arg-Ser-COOH<br>ALYRVRS | 3 |
| 7-mer La | NH$_2$-Asp-Ala-Tyr-Arg-Val-Arg-Ser-COOH<br>DAYRVRS | 4 |
| 7-mer Ya | NH$_2$-Asp-Leu-Ala-Arg-Val-Arg-Ser-COOH<br>DLARVRS | 5 |
| 7-mer Ra | NH$_2$-Asp-Leu-Tyr-Ala-Val-Arg-Ser-COOH<br>DLYAVRS | 6 |
| 7-mer Va | NH$_2$-Asp-Leu-Tyr-Arg-Ala-Arg-Ser-COOH<br>DLYRARS | 7 |
| 7-mer R2a | NH$_2$-Asp-Leu-Tyr-Arg-Val-Ala-Ser-COOH<br>DLYRVAS | 8 |
| 7-mer Sa | NH$_2$-Asp-Leu-Tyr-Arg-Val-Arg-Ala-COOH<br>DLYRVRA | 9 |
| *7-mer analogues created by "site specific replacement"* | | |
| 7-mer MK | NH$_2$-Asp-Leu-Tyr-Arg-Met-Lys-Ser-COOH<br>DLYRMKS | 10 |
| 7-mer KP | NH$_2$-Asp-Leu-Tyr-Lys-Val-Pro-Ser-COOH<br>DLYKVPS | 11 |
| 7-mer WI | NH$_2$-Asp-Leu-Trp-Arg-Ile-Arg-Ser-COOH<br>DLWRIRS | 12 |
| 7-mer IP | NH$_2$-Asp-Ile-Tyr-Arg-Val-Pro-Ser-COOH<br>DIYRVPS | 13 |
| 7-mer NV | NH$_2$-Asn-Val-Tyr-Arg-Val-Arg-Ser-COOH<br>NVYRVRS | 14 |

TABLE 1-continued

The present synthetic peptides

| Peptide Name. | Amino Acid Sequence | SEQ ID NO |
|---|---|---|
| 7-mer QK | NH₂-Asp-Leu-Tyr-Arg-Gln-Lys-Ser-COOH<br>DLYRQKS | 15 |
| 7-mer VFT | NH₂-Asp-Val-Phe-Arg-Val-Arg-Thr-COOH<br>DVFRVRT | 16 |
| 7-mer (V→L) | NH₂-Asp-Leu-Tyr-Arg-Leu-Arg-Ser-COOH<br>DLYRLRS | 17 |
| 7-mer (R2→Q) | NH₂-Asp-Leu-Tyr-Arg-Val-Gln-Ser-COOH<br>DLYRVQS | 18 |
| 7-mer (D→V) | NH₂-Val-Leu-Tyr-Arg-Val-Arg-Ser-COOH<br>VLYRVRS | 19 |
| 7-mer (D→F) | NH₂-Phe-Leu-Tyr-Arg-Val-Arg-Ser-COOH<br>FLYRVRS | 20 |
| 7-mer (D→L) | NH₂-Leu-Leu-Tyr-Arg-Val-Arg-Ser-COOH<br>LLYRVRS | 21 |
| Control Peptide (6-mer) | NH₂-Asp-Leu-Tyr-Arg-Val-Arg-COOH<br>DLYRVR | 22 |

The bold letter in any sequence indicates that particular amino acid is in D-form.

These synthesized peptides were then subject to MTT assay, in which vascular endothelial growth factor (VEGF) was used as a stimulant to induce cell proliferation. Results are depicted in FIGS. 1 to 4.

As evidenced from FIG. 1, VEGF (50 ng/ml) was able to induce the proliferation of RPMI8226 myeloma cell, and such proliferation was suppressed by the 7-mer (DLYRVRS), and similar results were found in the case when 7-mer Da, 7-mer La were respectively present. In contrast, 7-mer analogues in which alanine substitution were respectively made to 7-mer residues at positions 3, 4, 5, 6, and 7, caused loss of the inhibitory activity, suggesting the essential of the side chain in specific residues for the bioactivity of the 7-mer. The alanine substitution for the 7-mer residues at positions 1 and 2 (the alanine containing 7-mer peptides Da and La) sustained part of the 7-mer activity. The results indicate that both substitutions at position 1 (alanine (A) for aspartic acid (D)) and position 2 (alanine (A) for leucine (L)) of the 7-mer peptide have relatively little effect on proliferation suppressing activity and the main chain flexibility of position 1 and 2 may provide sites for 7-mer modification.

Figure 2:
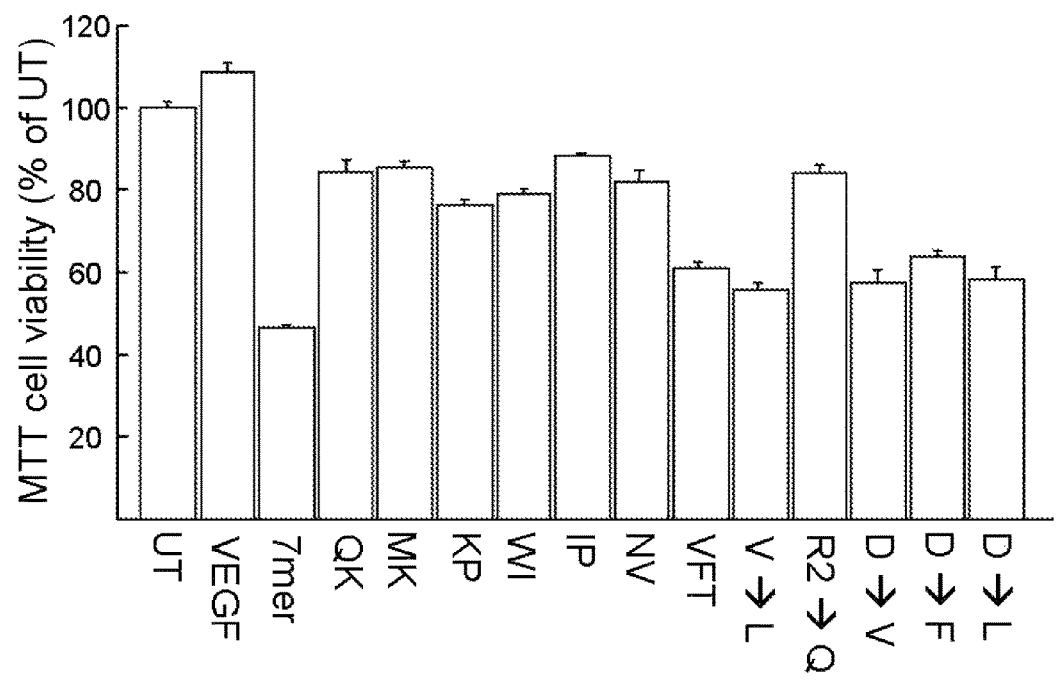
FIG. 2 is a bar graph illustrating the effects of the present 7-mer analogues created by site specific replacements on the VEGF-induced proliferation of RPMI8226 cells in accordance with one embodiment of the present disclosure, three independent assays were performed, and data is presented as the mean±S.D.

To further investigate the main chain flexibility in 7-mer, site specific amino acid substitutions in 7-mer were performed and the results are depicted in FIG. 2. The results indicated that each of the 7-mer analogues created by site specific replacements, which included 7-mer QK, 7-mer MK, 7-mer KP, 7-mer WI, 7-mer IP, 7-mer NV, 7-mer VFT, 7-mer (V→L), 7-mer (R2→Q), 7-mer (D→V), 7-mer (D→F), and 7-mer (D→L), could sustain 7-mer bioactivity, only partly.

Figure 3:
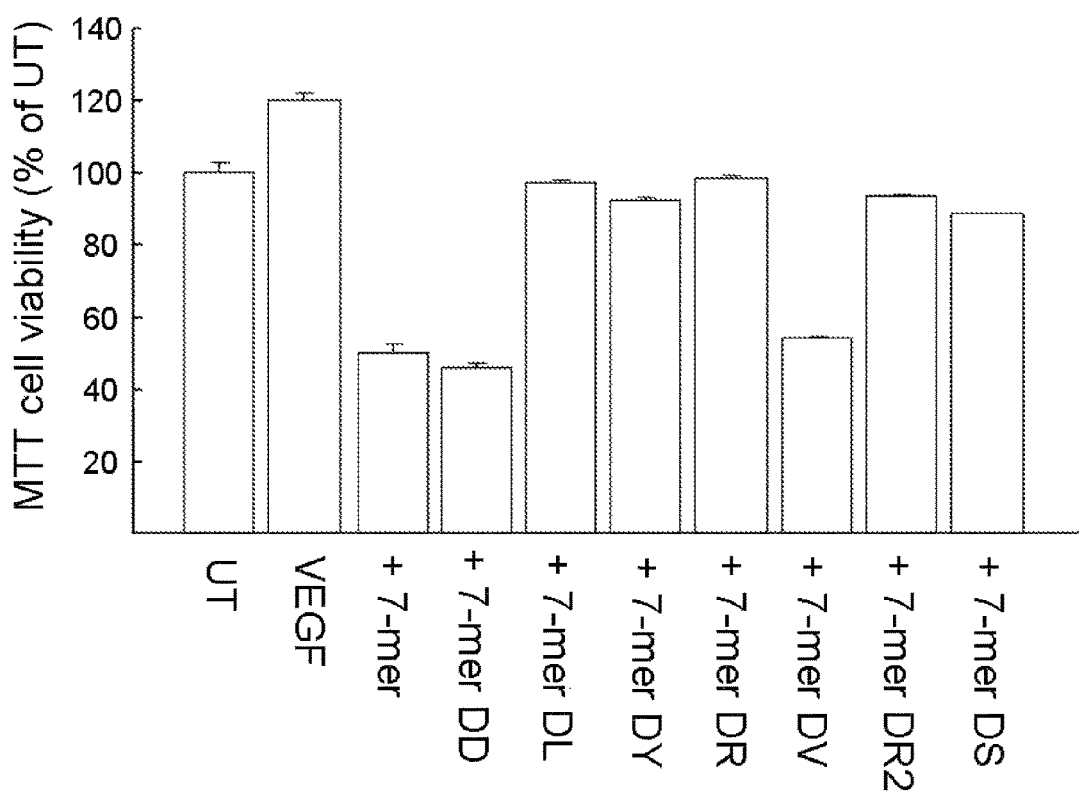
FIG. 3 is a bar graph illustrating the effects of the 7-mer analogues created by the D-form amino acid substitutions on the VEGF-induced proliferation of RPMI8226 cells in accordance with one embodiment of the present disclosure, three independent assays were performed, and data is presented as the mean ±S.D.
Figure 4:
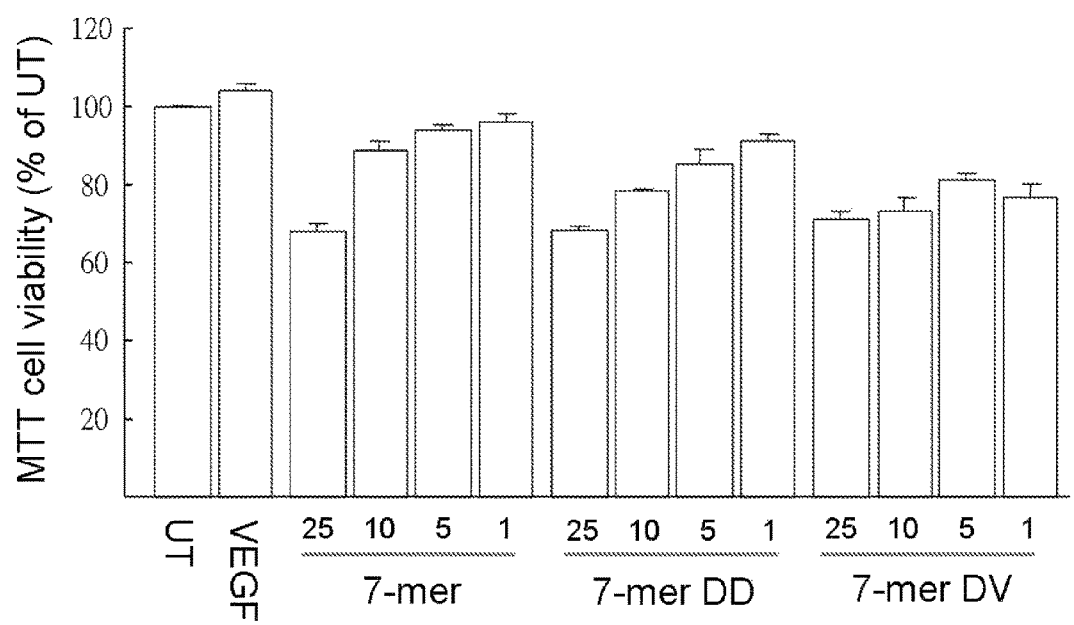
FIG. 4 illustrates the dose-dependent effect of 7-mer, 7-mer DD, and 7-mer DV on the VEGF-induced proliferation of RPMI8226 cells in accordance with one embodiment of the present disclosure, three independent assays were performed, and data is presented as the mean±S.D.

As to the 7-mer analogues that were created by substituting the natural L-form amino acids with their D-form counterparts, it was found that D-form amino acid substitution for the 7-mer residues at positions 2, 3, 4, 6, and 7 caused loss of the inhibitory activity (FIG. 3). Only D-amino acid substitutions made to the 7-mer residues at positions 1 (D-aspartic acid for L-aspartic acid) and 5 (D-valine for L-valine) still possessed the activity for suppressing VEGF-induced proliferation. Further investigation on the capability of the 7-mer, 7-mer DD and 7-mer DV in suppressing VEGF-induced cell proliferation revealed that the each peptides exerted its inhibitory action in a dose dependent manner (1 to 25 μM) (FIG. 4).

Taken together, the results of this example indicated that the amino acid residues at positions 1 and 2 of the 7-mer are not critical in terms of its ability of suppressing VEGF-induced cell proliferation; and the amino acid residues at positions 1 and 5 of the 7-mer can be either in L-form or in D-form, whereas the rest of the amino acid residues (i.e., residues at positions 2, 3, 4, 6, and 7 of the 7-mer) must remain in L-forms.

Example 2

The Present Synthetic Peptide Suppresses VEGF-induced Angiogenesis

In this example, the effect of the present synthetic peptides on VEGF-induced proliferation of HUVECs and tube formation were investigated. Results are summarized in Tables 2 and 3; and FIGS. 5 and 6.

TABLE 2

Effects of the present synthetic peptide on VEGF-induced cell proliferation in HUVECs

| Treatment | Cell number (Fold) | Treatment | Cell number (Fold) |
|---|---|---|---|
| Untreated | 1.00 ± 0.068 | VEGF + 7-mer MK | 1.04 ± 0.062** |
| VEGF (10 ng/mL) | 1.62 ± 0.070* | VEGF + 7-mer KP | 1.02 ± 0.075** |
| VEGF + 7-mer | 0.95 ± 0.050** | VEGF + 7-mer WI | 0.91 ± 0.078** |
| VEGF + 7-mer DD | 0.90 ± 0.048** | VEGF + 7-mer IP | 1.05 ± 0.067** |

TABLE 2-continued

Effects of the present synthetic peptide on VEGF-induced cell proliferation in HUVECs

| Treatment | Cell number (Fold) | Treatment | Cell number (Fold) |
|---|---|---|---|
| VEGF + 7-mer DY | 1.63 ± 0.077 | VEGF + 7-mer NV | 1.01 ± 0.086** |
| VEGF + 7-mer DV | 0.99 ± 0.078** | VEGF + 7-mer (V→L) | 1.02 ± 0.049** |
| VEGF + 7-mer DS | 1.59 ± 0.084 | VEGF + 7-mer QK | 1.09 ± 0.067** |

The concentration of the present synthetic peptide was 25 µM.
Data are expressed as mean ± S.E. of 3 experiments carried out in duplicate.
*p < 0.001 vs. untreated HUVECs;
**p < 0.05 vs VEGF-treated HUVECs.

As evidenced from Table 2, VEGF significantly enhanced the proliferation of HUVECs (1.62-folds as compared to that of the untreated control, P<0.001), and such VEGF-induced cell proliferation was suppressed by the addition of the present synthetic peptide (i.e., 7-mer and/or its analogues) except for the condition when 7-mer DS was added.

Figure 5:
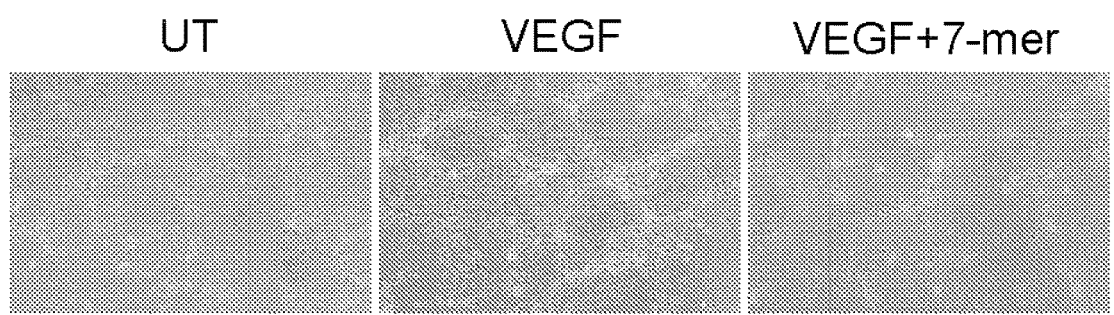
FIG. 5 are photographs depicting the effect of 7-mer on endothelial cells forming capillary like tubular structure in matrigel in accordance with one embodiment of the present disclosure.

During angiogenesis, endothelial cells form capillary tube-like structures, therefore tube formation is a useful indicator for evaluating whether an agent does possess antiangiogenic efficacy. As depicted in FIG. 5, a massive tube-like network was observed in HUVECs treated with VEGF for 6 hrs, as compared with that of the untreated (UT) HUVECs; and such VEGF-induced tube formation was inhibited when the present 7-mer peptide was present. Effects of the present synthetic peptides on VEGF-induced tube formation are summarized in Table 3.

TABLE 3

Effects of the present synthetic peptide on VEGF-induced HUVECs tube formation

| Treatment | Tube length (Fold) | Treatment | Tube length (Fold) |
|---|---|---|---|
| untreated | 1.00 ± 0.10 | VEGF + 7-mer MK | 1.18 ± 0.31** |
| VEGF (10 ng/mL) | 3.43 ± 0.32* | VEGF + 7-mer KP | 1.62 ± 0.29** |
| VEGF + 7-mer | 1.24 ± 0.23** | VEGF + 7-mer WI | 1.23 ± 0.22** |
| VEGF + 7-mer DD | 1.33 ± 0.25** | VEGF + 7-mer IP | 1.66 ± 0.20** |
| VEGF + 7-mer DV | 1.24 ± 0.18** | VEGF + 7-mer NV | 1.41 ± 0.32** |
| VEGF + 7-mer DS | 3.45 ± 0.26 | VEGF + 7-mer (V→L) | 1.41 ± 0.37** |
| | | VEGF + 7-mer QK | 1.46 ± 0.31** |

The concentration of the present synthetic peptide was 25 µM.
Quantification of the average tubular length was determined by image analysis software.
Data is presented in mean ± S.E. from four independent experiments.
*P < 0.0001 versus untreated HUVECs;
**P < 0.05 versus VEGF-treated HUVECs.

Similar to the findings in Table 2, VEGF significantly promoted tube formation, and such VEGF-induced tube-formation was suppressed by the addition of the present synthetic peptide (i.e., 7-mer and/or its analogues) except for the condition when 7-mer DS was added.

Figure 6:
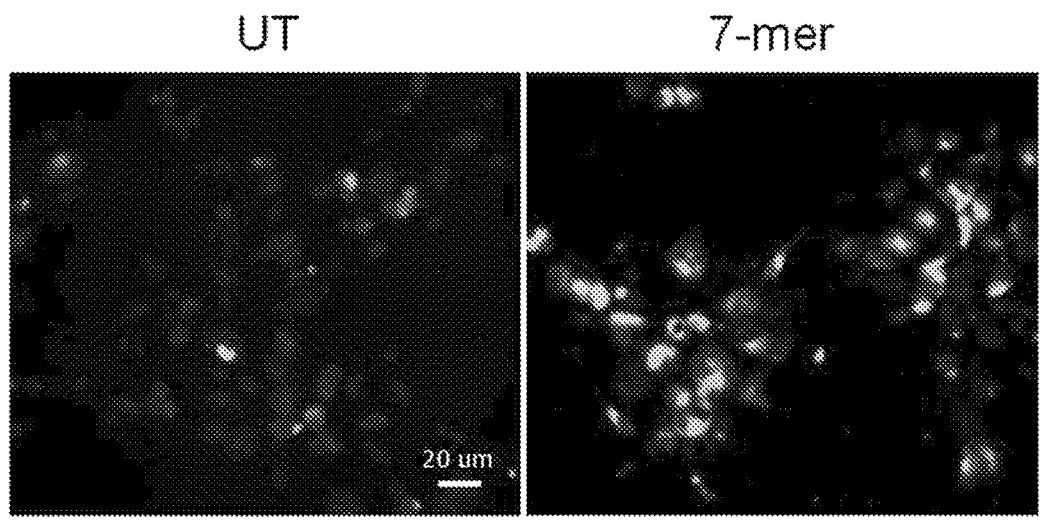
FIG. 6 illustrates the effect of the 7-mer on the induced apoptosis of HUVECs in accordance with one embodiment of the present disclosure.
Figure 6:
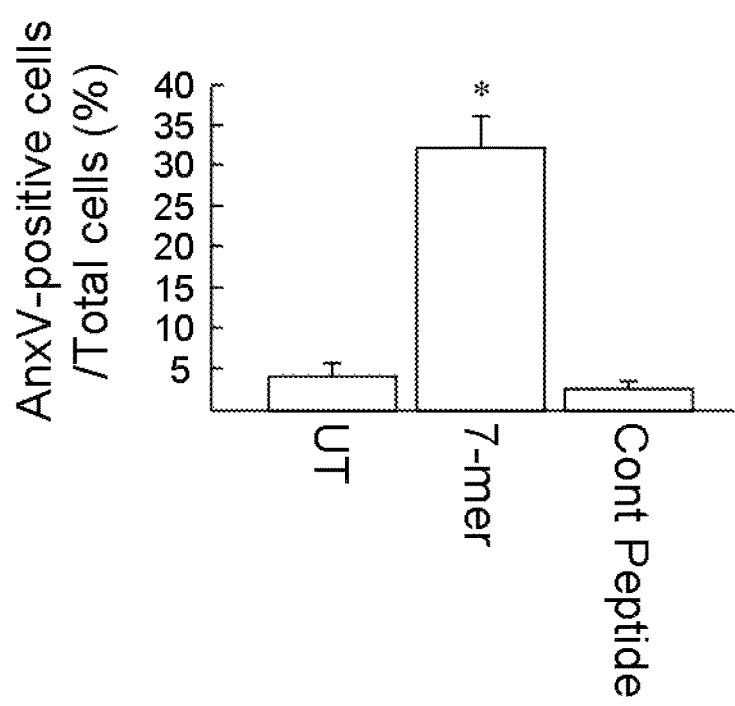

To determine whether the 7-mer anti-angiogenic activity is associated with cell apoptosis, quantification of apoptosis by annexin V-conjugated FITC staining indicated that treatment of 7-mer peptide for 16 hrs would increase the percentage of apoptotic HUVECs from 4.2±1.66% (UT; untreated) to 32.4±3.8% (FIG. 6). Control peptide (SEQ ID NO: 22), which was a 6-mer formed by deleting the serine (S) residue from the C-terminal of the 7-mer (SEQ ID NO: 2), did not result in cell apoptosis.

Taken together, the data suggests that the present synthetic peptides exert antiangiogenic activity by arresting VEGF-mediated capillary morphogenesis and inducing endothelial cell apoptosis; and the leucine (L), tyrosine (Y), arginine (R) and serine (S) residues of the 7-mer must be kept in their respective nature forms, otherwise the present synthetic peptide will lose its antiangiogenic efficacy when these three nature L-form amino acids are independently replaced by their corresponding D-form residues.

Example 3

Figure 7:
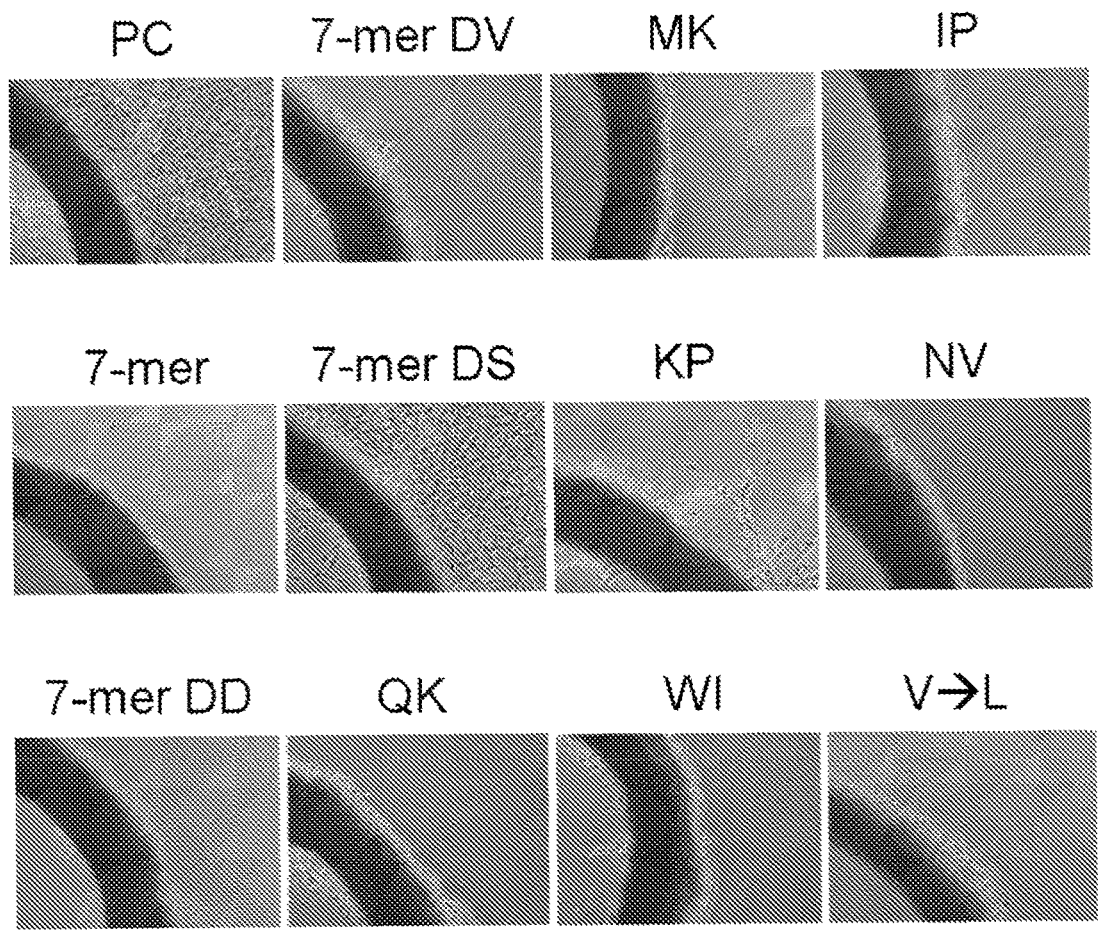
FIG. 7 are photographs of depicting the effects of the present synthetic peptide on VEGF-induced microvessel sprouting in rat aortic ring in accordance with one embodiment of the present disclosure.
Figure 8:
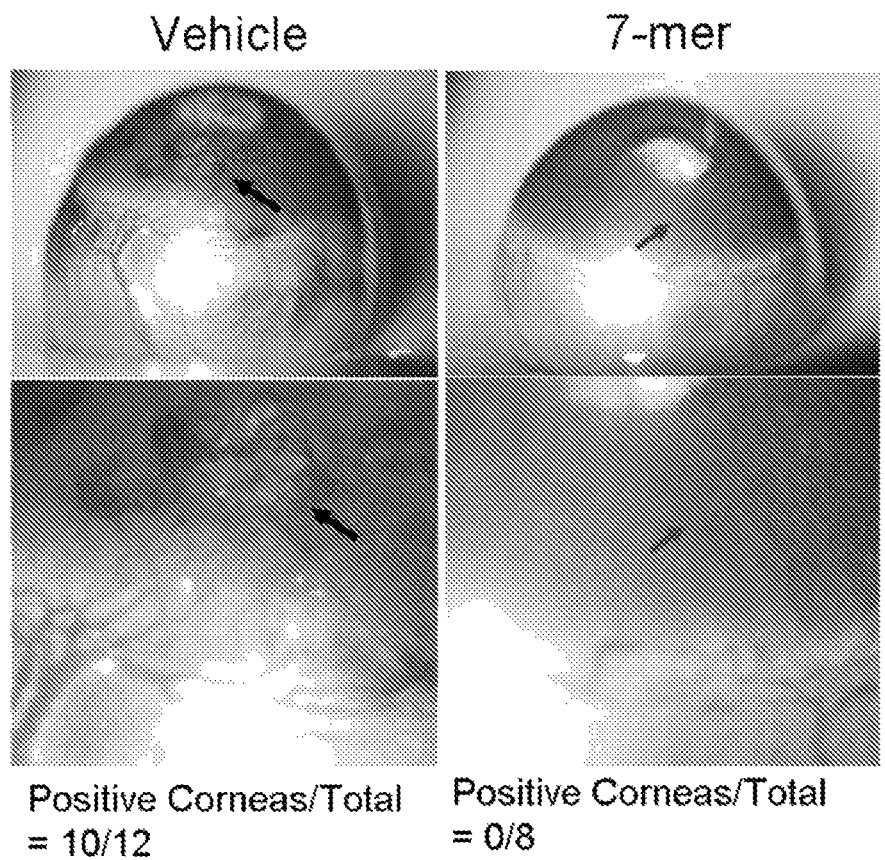
FIG. 8 are photographs illustrating the effects of 7-mer peptide on VEGF-induced corneal neovascularization in accordance with one embodiment of the present disclosure.

The Present Synthetic Peptides Inhibit Ex Vivo Microvessel Sprouting and In Vivo VEGF-induced Corneal Neovascularization The anti-angiogenic efficacy of the present synthetic peptides, was further investigated by, ex vivo microvessel sprouting assay, and in vivo VEGF-induced corneal neovascularization assay, in accordance with the procedures described in the section of "Material and Methods." Results are depicted in FIGS. 7 and 8.

The results of ex vivo microvessel sprouting assay are presented in the photographs of FIG. 7, in which significant level of sprouting microvessels was found around the aortic ring treated with beta-FGF alone (PC; positive control), and the level of sprouting microvessels was inhibited by the addition of the present 7-mer peptides (50 µM), including 7-mer DD, 7-mer DV, 7-mer MK, 7-mer KP, 7-mer WI, 7-mer IP, 7-mer NV, 7-mer (V→L), and 7-mer QK. The results are also consistent with the findings in Example 2, in which the sprouting phenomena around the ring was unaffected by 7-mer DS, where the tyrosine (Y), serine and the first arginine (R) of the present 7-mer peptide (SEQ ID NO: 2) were independently replaced by their respective D-form residues.

Results from the in vivo VEGF-induced corneal neovascularization assay are depicted in FIG. 8. In this in vivo corneal assay, VEGF (200 ng) was capable of inducing significant level of neovascularization in the cornea of C57BL/6 mice; however, such VEGF-induced neovascularization was completely abolished by the treatment of the present 7-mer peptide (2.5 µg).

Example 4

The Present Synthetic Peptide Suppresses In Vivo Growth of Uterine Sarcoma

Figure 9:
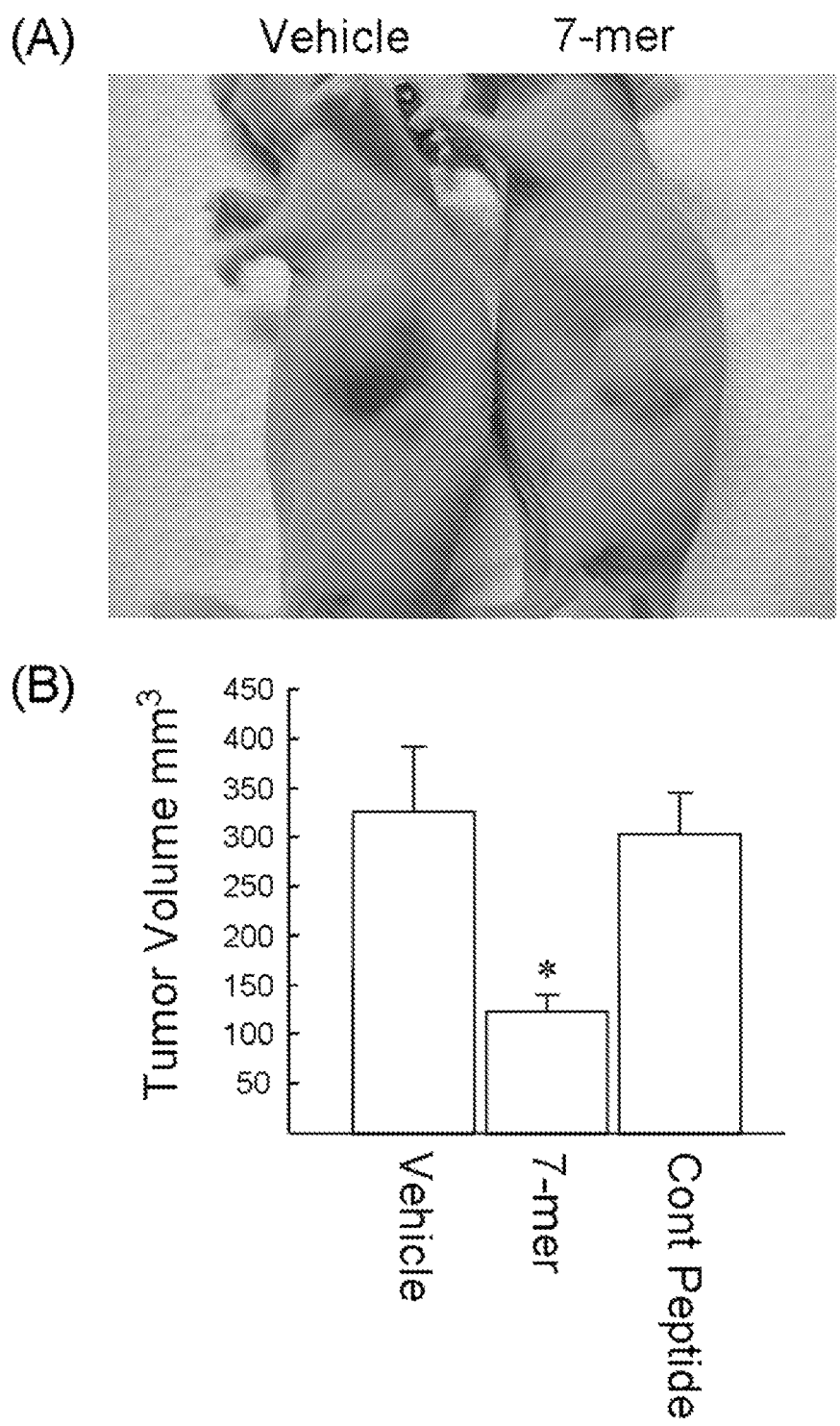
FIG. 9 illustrates the effects of the 7-mer peptide on the growth of xenografted human uterine sarcoma in accordance with one embodiment of the present disclosure.

In this example, the efficacy of the present synthetic peptides of example 1 on uterine sarcoma, which has been suggested to be resulted from the action of vascular endothelial growth factor (VEGF), was investigated. To this purpose, human uterine sarcoma cells (MES-SA/Dx5) were implanted in nude mice to induce tumor formation, and when the volume of each tumor reached 80 mm$^3$, animals were then treated with vehicle alone, or the 7-mer peptide at the dose of 10 mg/kg, every 2 days for 10 days. Results are depicted in FIG. 9.

As expected, tumors in animals treated with the present 7-mer peptide were significantly smaller than those receiving DMSO vehicle (125±15.4 versus 327±64.2 mm$^3$; FIG. 9). Further, the respective sizes of tumors in animals treated with the control peptide, which has the sequence of DLYRVR (SEQ ID NO: 22) remained relatively unchanged, as well as the body weight of each animals. The results from this example confirmed the in vivo efficacy of the present 7-mer synthetic peptide on the growth of sarcoma tissues.

Example 5

The Present Synthetic Peptide Suppresses In Vivo Lung Cancer Metastasis

Metastasis is the foremost cause of death from cancer. In this example, to investigate the efficacy of the present synthetic peptide on the metastasis of cancer cells, B16-F10 cells were injected into the tail vein of a mouse, the animal was then treated with the present synthetic peptide (7-mer or 7-mer DD, 10 mg/Kg) by intraperitoneal injections every 2 days. Upon completion of the experiment, the lungs were then removed and the tumor colonies visible to the eyes were then counted. Results are depicted in FIG. 10.

Figure 10:
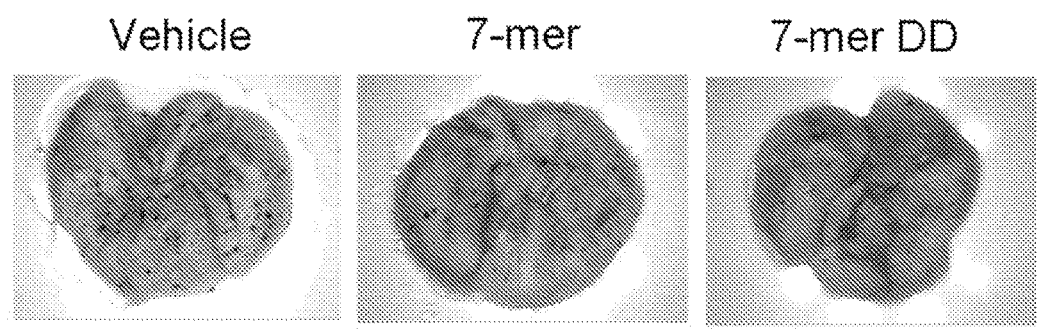
FIG. 10 are photographs depicting the effects of the 7-mer, and 7-mer DD peptide on the metastasis of B16-F10 melanoma cells in accordance with one embodiment of the present disclosure.

As depicted in FIG. 10, both the 7-mer and the 7-mer DD were capable of reducing the number of colonies formed on the surface of the lung, whereas the vehicle treatment did not possess such effect. Results obtained by other synthetic peptides (10 mg/Kg) including 7-mer DL, 7-mer DR, 7-mer DV, 7-mer MK, 7-mer KP, 7-mer WI, 7-mer IP, 7-mer NV, 7-mer (V→L), and 7-mer QK were summarized in Table 4.

TABLE 4

Effects of the present synthetic peptide on in vivo metastasis of lung cancer cells

| Treatment | No. lung colonies | Inhibition (%) |
|---|---|---|
| vehicle | 225 ± 39.3 | |
| 7-mer | 72 ± 16.0* | 67.9 |
| 7-mer DD | 40 ± 15.7* | 82.3 |
| 7-mer DV | 51 ± 17.0* | 77.4 |
| 7-mer DS | 245 ± 30.4 | −9.0 |
| 7-mer MK | 79 ± 26.4* | 65.0 |
| 7-mer KP | 69 ± 11.5* | 69.3 |
| 7-mer WI | 74 ± 24.3* | 67.3 |
| 7-mer IP | 63 ± 9.4* | 72.0 |
| 7-mer NV | 55 ± 16.5* | 75.8 |
| 7-mer (V→L) | 75 ± 30.4* | 66.8 |
| 7-mer QK | 82 ± 16.3* | 63.5 |

Data are expressed as mean ± S.E. (n = 5).
*P < 0.05 versus vehicle treated mice.

Taken together, the results indicate that the present synthetic peptides including 7-mer, 7-mer DD, 7-mer DV, 7-mer MK, 7-mer KP, 7-mer WI, 7-mer IP, 7-mer NV, 7-mer (V→L), and 7-mer QK, may suppress in vivo metastasis of cancerous cells.

Example 6

The Present Synthetic Peptide Prevents the Breakdown of In Vivo Blood-Retinal Barrier in Diabetic Animals Diabetic retinopathy is characterized by blood-retinal barrier (BRB) breakdown and neurotoxicity. To evaluate the possible beneficial effect of the present synthetic peptides on diabetic retinopathy, STZ-induced diabetic mice were intraperitoneally injected with 7-mer peptide, DMSO vehicle or the control peptide (SEQ ID NO: 22). The retinal vascular abnormality was then monitored by detecting the extravasation of BSA-fluorescein. Results are depicted in FIG. 11.

Figure 11:
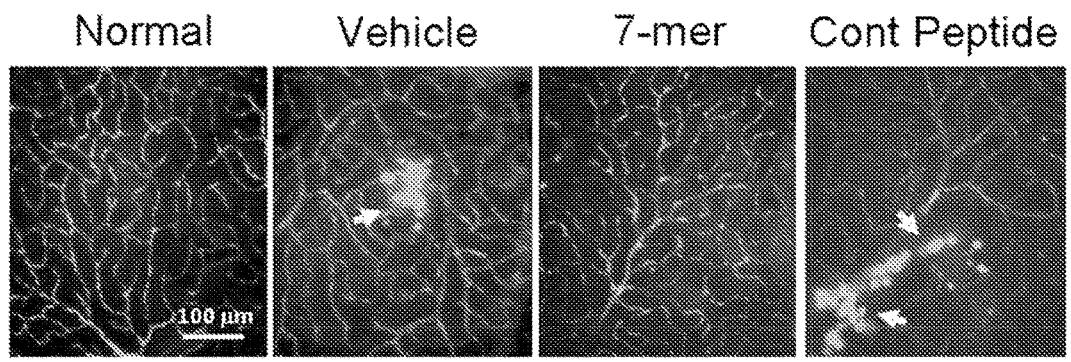
FIG. 11 illustrates the effects of the 7-mer peptide on vascular leakage in the retina of diabetic mice in accordance with one embodiment of the present disclosure, in which (A) are fluorescent images of a diabetic retina treated with vehicle, the control peptide or the 7-mer, the vascular lesions are indicated by the arrows, and the accumulation of FITC-BSA is an indication of hemorrhage; (B) is a bar graph of the quantified results of hemorrhaging area in the retina.
Figure 11:
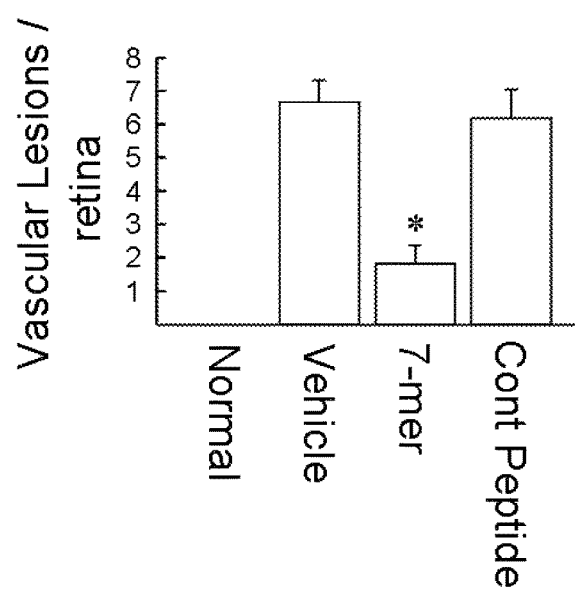

Microscopic images provided in FIG. 11 evidenced that vehicle or control peptide-treated diabetic mice had several hemorrhaging areas in the retinal parenchyma; and the hemorrhage was successfully blocked by the addition of the present synthetic peptide, in which the number of vascular lesions was significantly reduced as compared to that treated by the vehicle (1.8±0.54 versus 6.7±0.66, FIG. 11, panel B).

The amounts of leaked FITC-BSA in retinal was also quantitatively analyzed by determining the fluorescence intensity of leaked FITC-BSA in the entire retina tissue, and the results are summarized in Table 5.

TABLE 5

Effects of the present synthetic peptide on blood-retinal barrier in diabetic animals

| Treatment | Fluorescence Intensity (Fold) | Treatment | Fluorescence Intensity (Fold) |
|---|---|---|---|
| vehicle | 1 ± 0.10 | VEGF + 7-mer MK | 0.37 ± 0.095* |
| VEGF + 7-mer | 0.29 ± 0.076* | VEGF + 7-mer KP | 0.37 ± 0.13* |
| VEGF + 7-mer DD | 0.38 ± 0.11* | VEGF + 7-mer WI | 0.31 ± 0.085* |
| VEGF + 7-mer DV | 0.31 ± 0.072* | VEGF + 7-mer IP | 0.38 ± 0.12* |
| VEGF + 7-mer DS | 0.96 ± 0.12 | VEGF + 7-mer NV | 0.35 ± 0.11* |
| | | VEGF + 7-mer (V→L) | 0.33 ± 0.079* |
| | | VEGF + 7-mer QK | 0.31 ± 0.081* |

Data was expressed in mean ± SEM of 3 mice in each group.
*P < 0.05 versus vehicle-treated.

Results from table 5 confirmed that the present synthetic peptides including 7-mer, 7-mer DD, 7-mer DV, 7-mer MK, 7-mer KP, 7-mer WI, 7-mer IP, 7-mer NV, 7-mer (V→L), and 7-mer QK may significantly prevent the extravasation of FITC-BSA.

Figure 12:
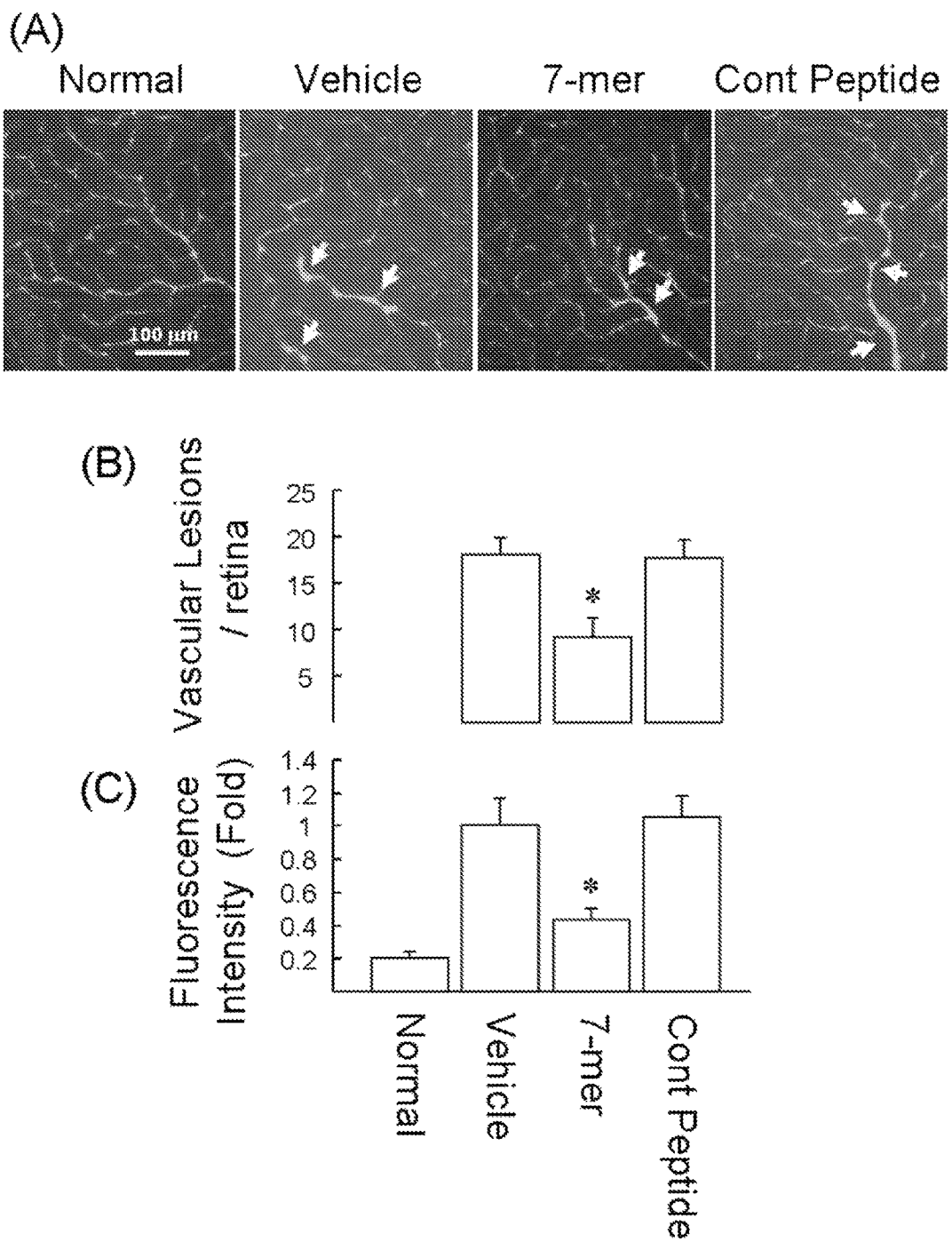
FIG. 12 illustrates the effects of the 7-mer peptide on vascular leakage in the retina of diabetic rats in accordance with one embodiment of the present disclosure, in which (A) are fluorescent images of a diabetic retina treated with vehicle, the control peptide or the 7-mer, the vascular lesions are indicated by the arrows, and the accumulation of FITC-BSA is an indication of hemorrhage; (B) is a bar graph depicting the quantified results of hemorrhaging area in the retina; and (C) is bar graph depicting the quantified results of the leaked FITC-BSA accumulated in the whole retina.

Further, diabetic animals often exhibited increased vascular lesions in the retinas, intravitreal injection of the 7-mer peptide reduced the number of vascular lesion in retina, as compared with that treated by vehicle only (9.2±2.15 versus 18.0±1.93; FIG. 12, panel B). Analysis of the fluorescence intensity of FITC-BSA in entire retina tissues also revealed a reduction in the levels of leaked FITC-BSA as compared with the vehicle treated control animal (0.43±0.07-fold; FIG. 12, panel C).

Taking together, the present synthetic peptides may prevent retinal vascular abnormality in diabetic animals.

Example 7

The Present Synthetic Peptide Suppresses Laser-Induced Choroidal Neovascularization (CNV)

Figure 13:
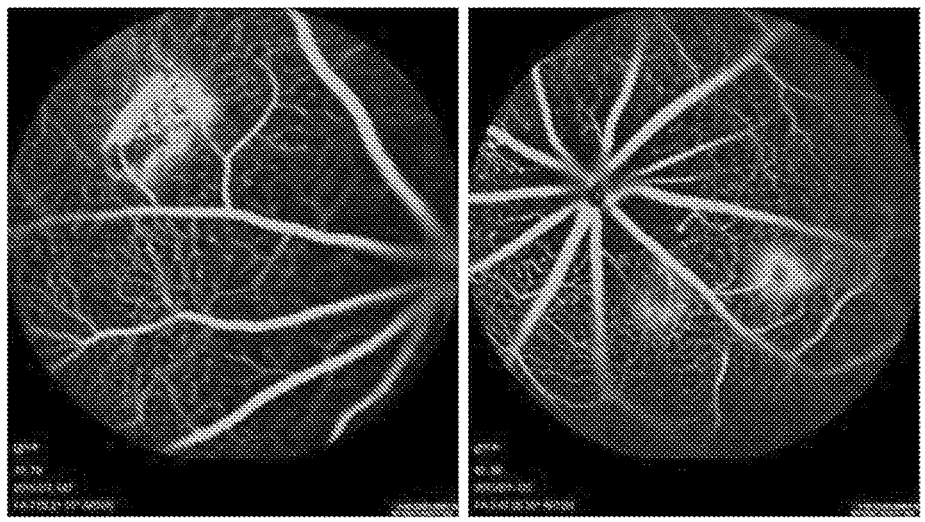
FIG. 13 illustrates the effects of the 7-mer peptide on laser damaged retina in accordance with one embodiment of the present disclosure, in which (A) are fundus fluorescein angiography illustrating the effects of the 70 mer peptide; and (B) is a bar graph depicting the quantified results of panel (A), in which the number of hemorrhaging area in the retina was evaluated by a retina specialist and presented in various fluorescein leakage grades, Grade 0: no hyperfluorescence, Grade 1: hyperfluorescence without leakage, Grade 2a: hyperfluorescence and late leakage, Grade 2b: bright hyperfluorescence and late leakage beyond treated areas.
Figure 13:
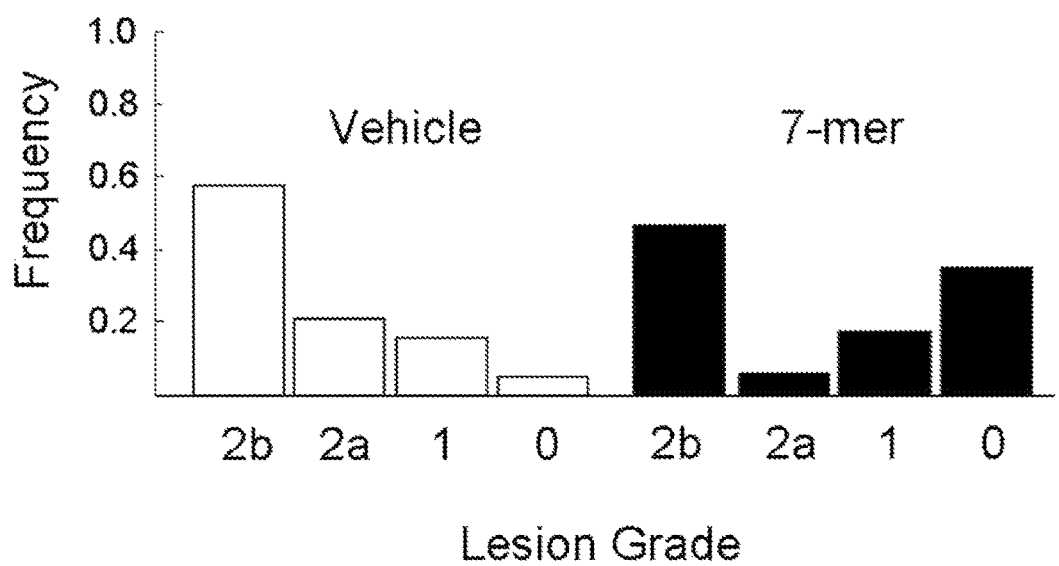

Wet type age-related macular degeneration (AMD) is characterized by extensive growth of new vessels in retina. One of the effective strategies for treating wet AMD is to limit the invasion of choroidal neovascularization (CNV). In the present example, the efficacy of the present synthetic peptide on preventing the invasion of CNV was investigated using laser-induced wet AMD mouse model in accordance with the procedures described in the "Material and Method" section. Newly formed microvessels with clear fluorescein leakage in retina were assessed by fundus fluorescein angiography 10 days post laser treatment, and results are provided in the photographs of FIG. 13. Further, results from the CNV lesion grades also indicated that a lower severity distribution of CNV was found in animals treated with the 7-mer synthetic peptide, as compared with that of the vehicle-treated animal. The distribution frequency remained relatively unchanged for 16 days after laser treatment further suggests that the 7-mer synthetic peptide does possess the capability of suppressing CNV generation.

Further, the effect of 7-mer or 7-mer DD on rat model of laser-induced wet AMD was also investigated. Fluorescein angiography images were obtained on day 14 after laser burn, and the images were subsequently scored. Results are depicted in FIG. 14.

Figure 14:
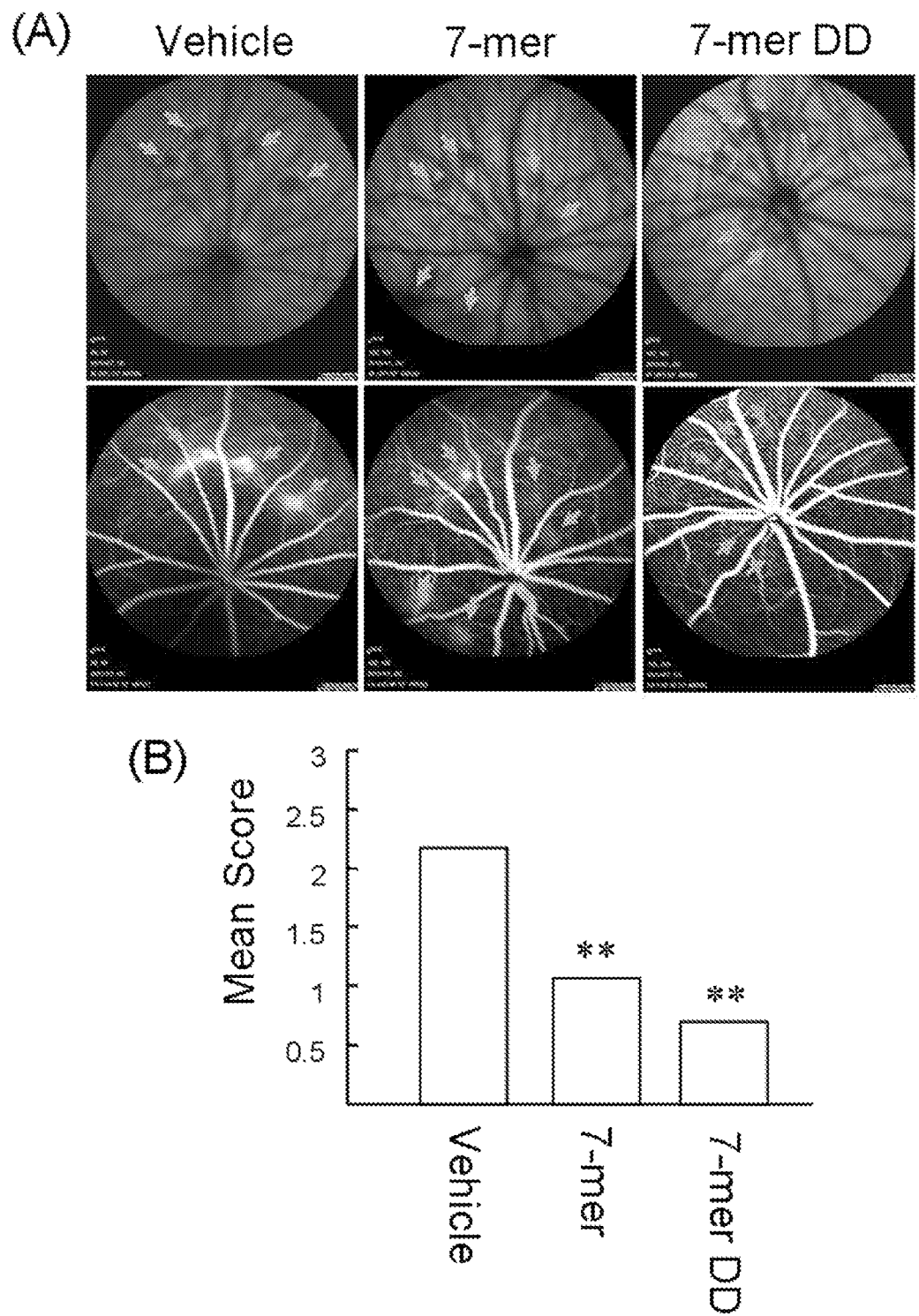
FIG. 14 depicts the effects of the present synthetic peptide on CNV lesions in rats in accordance with one embodiment of the present disclosure, in which (A) are photographs treated with vehicle, 7-mer, or 7-mer DD, arrows in the panels represent the laser spots, (B) is a bar graph depicting the quantitative results.

As depicted in FIG. 14, lesions caused by the laser burn were significantly ameliorated by the treatment of 7-mer or 7-mer DD, as compared with that treated by PBS vehicle. The data suggest that the present synthetic peptide is a promising therapy for CNV-related angiogenesis.

Taken together, the results presented in the afore-mentioned working examples confirm the short synthetic peptide of the present disclosure may be used for the treatment and/or prophylaxis of diseases or conditions related to angiogenesis.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of prophylactically treating or palliative treating a subject suffering from a disease or a condition related to angiogenesis comprising administering to the subject an effective amount of a synthetic peptide consisting of 7 consecutive amino acid residues set forth as $X_1X_2X_3X_4X_5X_6X_7$ (SEQ ID NO: 1), wherein, $X_1$ is alanine (A), aspartic acid (D), asparagine (N), leucine (L), phenylalanine (F), or valine (V);

$X_2$ is alanine (A), isoleucine (I), leucine (L), or valine (V);

$X_3$ is phenylalanine (F), tyrosine (Y) or tryptophan (W);

$X_4$ is arginine (R) or lysine (K);

$X_5$ is valine (V), methionine (M), isoleucine (I), leucine (L), or glutamine (Q);

$X_6$ is arginine (R), glutamine (Q), lysine (K) or proline (P);

$X_7$ is serine (S) or threonine (T); and each $X_2$, $X_3$, $X_4$, $X_6$ and $X_7$ are independently L-form amino acid residues;

the synthetic peptide has the amino acid sequence that is any of SEQ ID NOs: 2, 3, 4, 10, 11, 12, 13, 14, 15, 16, 17, 18, 19, 20 or 21; and the disease or a condition related to angiogenesis is an ocular disease selected from the group consisting of corneal neovascularization, choroidal neovascularization (CNV), VEGF-induced corneal neovascularization, wet-type age-related macular degeneration (AMD), and diabetic retinopathy.

2. The method of claim 1, wherein at least one of $X_1$ and $X_5$ is a D-form amino acid residue.

3. The method of claim 2, wherein $X_1$ is in D-form.

4. The method of claim 2, wherein $X_5$ is in D-form.

5. The method of claim 1, wherein the ocular disease is age-related macular degeneration (AMD).

6. The method of claim 1, wherein the ocular disease is diabetic retinopathy.

7. The method of claim 1, wherein the subject is a human.

* * * * *